(12) United States Patent
Curran et al.

(10) Patent No.: US 12,410,145 B2
(45) Date of Patent: Sep. 9, 2025

(54) EFFICIENT PROCESS FOR MAKING 6-CARBOXY BENZOXAZOLE DERIVATIVES

(71) Applicant: Pfizer Ireland Pharmaceuticals, New York, NY (US)

(72) Inventors: Simon Peter Curran, Frankfield (IE); Padraig Mary O'Neill, Crosshaven (IE)

(73) Assignee: Pfizer Inc., New York, NY (US)

( * ) Notice: Subject to any disclaimer, the term of this patent is extended or adjusted under 35 U.S.C. 154(b) by 656 days.

(21) Appl. No.: 17/757,740

(22) PCT Filed: Dec. 16, 2020

(86) PCT No.: PCT/IB2020/062040
§ 371 (c)(1),
(2) Date: Jun. 20, 2022

(87) PCT Pub. No.: WO2021/124158
PCT Pub. Date: Jun. 24, 2021

(65) Prior Publication Data
US 2023/0090609 A1    Mar. 23, 2023

Related U.S. Application Data

(60) Provisional application No. 63/120,426, filed on Dec. 2, 2020, provisional application No. 62/951,691, filed on Dec. 20, 2019.

(51) Int. Cl.
*C07D 263/57* (2006.01)
*C07D 493/18* (2006.01)

(52) U.S. Cl.
CPC ......... *C07D 263/57* (2013.01); *C07D 493/18* (2013.01)

(58) Field of Classification Search
CPC .................................................. C07D 263/57
See application file for complete search history.

(56) References Cited

U.S. PATENT DOCUMENTS 9,249,112 B2 * 2/2016 Labaudiniere .......... A61P 17/00
9,770,441 B1 * 9/2017 Girard ................... C07D 263/57

FOREIGN PATENT DOCUMENTS

| EP | 3453703 | 3/2019 | |
|----|---------|--------|---|
| WO | 2004056315 | 7/2004 | |
| WO | 2013168014 | 11/2013 | |
| WO | WO-2013168014 A1 * | 11/2013 | ........... A61K 47/542 |
| WO | 2016038500 | 3/2016 | |
| WO | 2021/124158 A1 | 6/2021 | |

OTHER PUBLICATIONS

Barbero, Margherita The efficient o-benzenedisulfonimide catalysed synthesis of benzothiazoles, benzoxazoles and benzimidazoles ARKIVOC 2012 (ix) 262-279.*

Francesco, Ferlin, et al., "Continuous flow/waste-minimized synthesis of benzoxazoles catalysed by heterogeneous manganese systems", Green Chemistry, Sep. 30, 2019, pp. 5298-5305, 21(19).

Gulluzar, Bastug, et al., "Functionalized Orthoesters as Powerful Building Blocks for the Efficient Preparation of Heteroaromatic Bicycles", Organic Letters, Jul. 6, 2012, pp. 3502-3505, 14(13).

Jonckers, Tim H.M., et al., "Benzoxazole and benzothiazole amides as novel pharmacokinetic enhancers of HIV protease inhibitors", Bioorganic & Medicinal Chemistry Letters, Jun. 10, 2012, pp. 4998-5002, 22(15).

Kanoh, Shigeyoshi, et al., "Isomerization of cyclic ethers having a carbonyl functional group: new entries into different heterocyclic compounds", Tetrahedron, Aug. 26, 2002, pp. 7049-7064, 58(35).

Kun-Ming, Liu, et al., "Room-temperature cobalt-catalyzed arylation of aromatic acids: overriding the ortho-selectivity via the oxidative assembly of carboxylate and aryl titanate reagents using oxygen", Organic & Biomolecular Chemistry, Jan. 2016, pp. 1593-1598, 14(5).

(Continued)

*Primary Examiner* — David K O'Dell
(74) *Attorney, Agent, or Firm* — John A. Wichtowski

(57) ABSTRACT

The present invention is directed to an efficient process for preparing benzoxazole derivatives comprising the step of reacting a 4-Amino-3-hydroxybenzoic acid compound of Formula III with a 3,5-Dichlorophenyl ortho ester compound of Formula II to provide the compound of Formula I

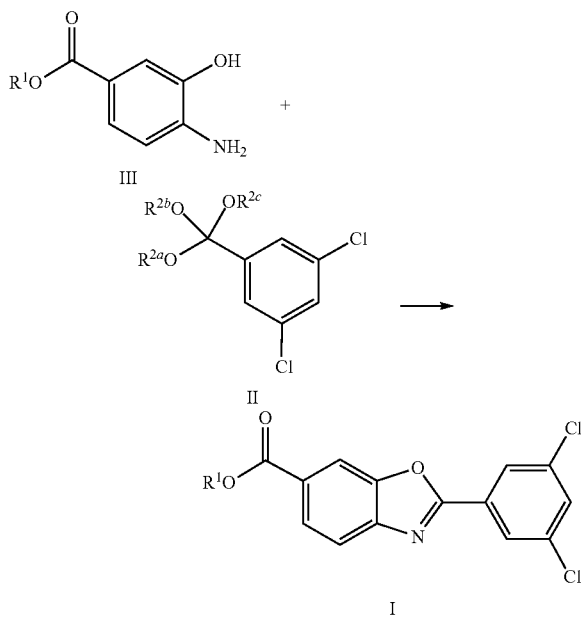

wherein $R^1$, $R^{2a}$, $R^{2b}$ and $R^{2c}$ are as described herein.

33 Claims, 1 Drawing Sheet

(56) References Cited

OTHER PUBLICATIONS

Shi, Yajie, et al., "Iridium-catalyzed intramolecular C—N and C—O/S cross-coupling reactions: Preparation of benzoazole, derivatives", Tetrahedron Letters, Aug. 26, 2019, pp. 7, 60(40).
Yamamoto, Takuya, et al., "Nickel-Catalyzed C—H Arylation of Azoles with Haloarenes: Scope, Mechanism, and Applications to the Synthesis of Bioactive Molecules", Chemistry, A European Journal, Aug. 29, 2011, pp. 10113-10122, 17(36).
Zhang, Yong, et al., "Iodine Promoted One-Pot Synthesis of 2-Aryl Benzoxazoles from Amidoximes via Oxidative Cyclization and Ring Contraction", European Journal of Organic Chemistry, Nov. 21, 2019, pp. 7506-7510, 2019 (45).
Green, T.W., et al., "Protection for the Carboxyl Group" Chapter 5, pp. 152-192,. Https;//doi.org/10.1002/0471220574.ch5 Sep. 4, 1999.
India Application No. 202217035311, Examination Report, mailed Nov. 15, 2022, 8 pages.
PCT Application No. PCT/IB2020/062040, filed Dec. 16, 2022, International Preliminary Report on Patentability and Written Opinion, International Searching Authority, mailed on May 17, 2022, 11 pages.
Wipf, P., et al., "Synthetic applications of ortho esters", Pure and Applied Chemistry, 1999, pp. 315-421, 71(3).
International Preliminary Report on Patentability issued in PCT/IB2020/062040; mailed on Jun. 30, 2022; 12 pp.
International Search Report issued in PCT/IB2020/062040; mailed on Feb. 16, 2021; 7 pp.
Written Opinion issued in PCT/IB2020/062040; mailed on Feb. 16, 2021; 10 pp.

\* cited by examiner

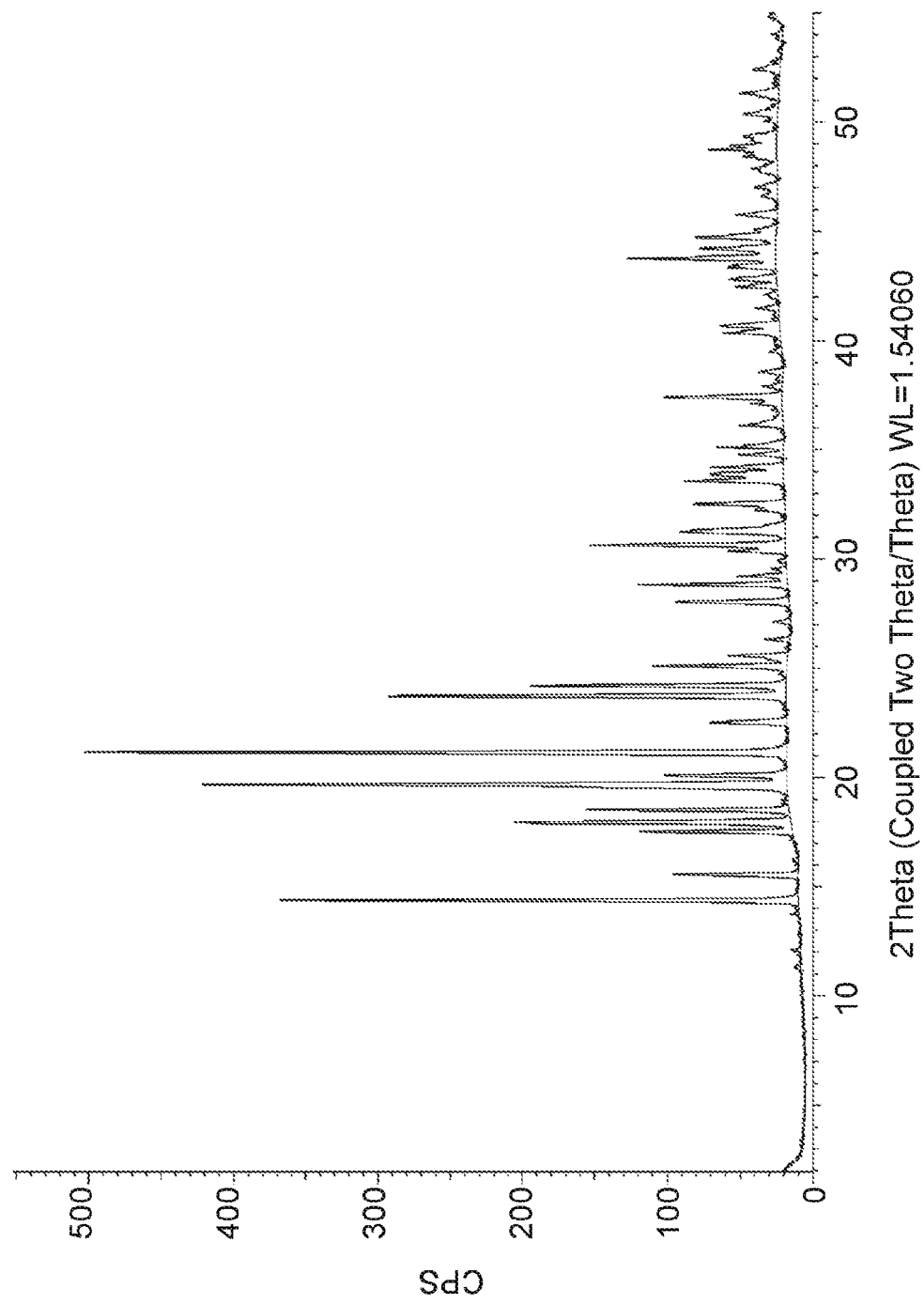

US 12,410,145 B2

EFFICIENT PROCESS FOR MAKING 6-CARBOXY BENZOXAZOLE DERIVATIVES

This application is a national stage application under 35 U.S.C. 371 of PCT/IB2020/062040, filed on Dec. 16, 2020, which claims the benefit of U.S. Provisional Patent Application No. 63/120,426, filed on Dec. 2, 2020 and U.S. Provisional Patent Application No. 62/951,691, filed on Dec. 20, 2019, the disclosures of which are hereby incorporated by reference in their entirety.

FIELD OF THE INVENTION

The present invention relates to a process for making a benzoxazole derivative transthyretin stabilizer or a pharmaceutically acceptable salt thereof. Particularly, the present invention relates to a process of making a 2-(3,5-dichlorophenyl)-1,3-benzoxazole-6-carboxylic acid derivative or a pharmaceutically acceptable salt thereof by reacting 4-amino-3-hydroxybenzoic acid or a carboxyl protected derivative thereof with an appropriate 3,5-dichlorophenyl orthoester compound. The processes of the invention are particularly useful in preparing 2-(3,5-dichlorophenyl)-1,3-benzoxazole-6-carboxylic acid or a pharmaceutically acceptable salt thereof which is useful in stabilizing transthyretin, inhibiting transthyretin misfolding, proteolysis, and treating amyloid diseases associated thereto.

BACKGROUND OF THE INVENTION

Transthyretin (TTR) is a 55 kDa homotetrameric protein present in serum and cerebral spinal fluid and which functions as a transporter of L-thyroxine (T4) and holo-retinol binding protein (RBP). TTR has been found to be an amyloidogenic protein that, under certain conditions, can be transformed into fibrils and other aggregates which can lead to disease pathology such as polyneuropathy or cardiomyopathy in humans.

U.S. Pat. Nos. 7,214,695; 7,214,696; 7,560,488; 8,168,683; and 8,653,119 each of which is incorporated herein by reference, discloses benzoxazole derivatives which act as transthyretin stabilizers and are of the formula

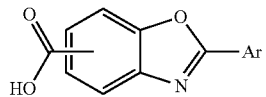

or a pharmaceutically acceptable salt thereof; wherein Ar is 3,5-difluorophenyl, 2,6-difluorophenyl, 3,5-dichlorophenyl, 2,6-dichlorophenyl, 2-(trifluoromethyl)phenyl or 3-(trifluoromethyl)phenyl and processes for making these compounds. Particularly, 2-(3,5-dichlorophenyl)-1,3-benzoxazole-6-carboxylic acid (tafamidis) of the formula

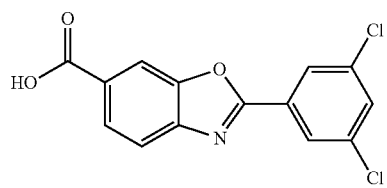 [SMILES: O=C(O)c1ccc2nc(-c3cc(Cl)cc(Cl)c3)oc2c1]

and processes for making it are disclosed therein. Tafamidis is an orally active transthyretin stabilizer that inhibits tetramer dissociation and proteolysis that has been approved in certain jurisdictions for the treatment of transthyretin polyneuropathy (TTR-PN) and for the treatment of transthyretin cardiomyopathy (TTR-CM). U.S. Pat. No. 9,249,112 and U.S. Patent Application Publication No. US 2019/0119226, also incorporated herein by reference, disclose polymorphic forms of the meglumine salt of 2-(3,5-dichlorophenyl)-1,3-benzoxazole-6-carboxylic acid (tafamidis meglumine). U.S. Pat. No. 9,770,441 discloses polymorphic forms of the free acid of 2-(3,5-dichlorophenyl)-1,3-benzoxazole-6-carboxylic acid (tafamidis), is also incorporated by reference herein. There is a continuing need to provide efficient synthetic processes for making 2-(3,5-dichlorophenyl)-1,3-benzoxazole-6-carboxylic acid derivatives, pharmaceutically acceptable salts thereof and polymorphic forms of the 2-(3,5-dichlorophenyl)-1,3-benzoxazole-6-carboxylic acid derivatives and pharmaceutically acceptable salts thereof.

SUMMARY OF THE INVENTION

The present invention is directed to a process for preparing a 6-Carboxy-2-(3,5-dichlorophenyl)benzoxazole compound of Formula I

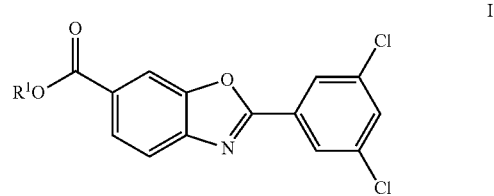

the process comprising the step of reacting a 4-Amino-3-hydroxybenzoic acid compound of Formula III with a 3,5-Dichlorophenyl ortho ester compound of Formula II to provide the compound of Formula I

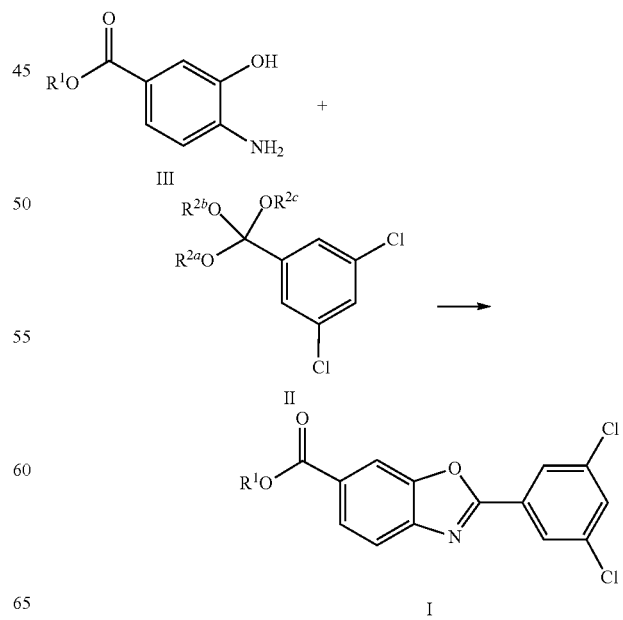

wherein R¹ is hydrogen or a carboxyl protecting group; and R²ᵃ, R²ᵇ and R²ᶜ are each independently $C_1$-$C_6$alkyl or any two of R²ᵃ, R²ᵇ and R²ᶜ taken together are a $C_1$-$C_6$alkanediyl or R²ᵃ, R²ᵇ and R²ᶜ taken together are a $C_3$-$C_{10}$alkanetriyl. The process of the invention for making the compounds of Formula I can be carried out in an appropriate solvent or in certain instances where the compound of Formula II is an oil no additional solvent may be required. The process of the invention may be carried out in the presence of an acid catalyst, a base catalyst or no catalyst and the process can be carried out from 0° C. to the reflux temperature of the solvent used with the process being carried out over a period of 15 minutes to multiple days. The processes of the invention also comprise further steps such as isolating the compounds of Formula I or Ia and preparing polymorphic forms of the compounds of Formula I or Ia.

BRIEF DESCRIPTION OF THE DRAWINGS

FIG. 1: PXRD spectrum of crystalline 1-(3,5-dichlorophenyl)-4-methyl-2, 6, 7-trioxabicyclo[2.2.2]octane

DETAILED DESCRIPTION OF THE INVENTION

A first embodiment of the present invention, designated E1, is a process for preparing a 6-Carboxy-2-(3,5-dichlorophenyl)benzoxazole compound of Formula I

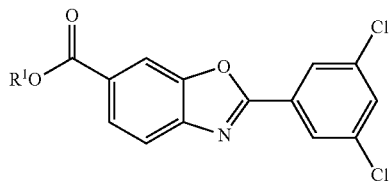

I the process comprising reacting a 4-Amino-3-hydroxybenzoic acid compound of Formula III with a 3,5-Dichlorophenyl ortho ester compound of Formula II to provide the compound of Formula I

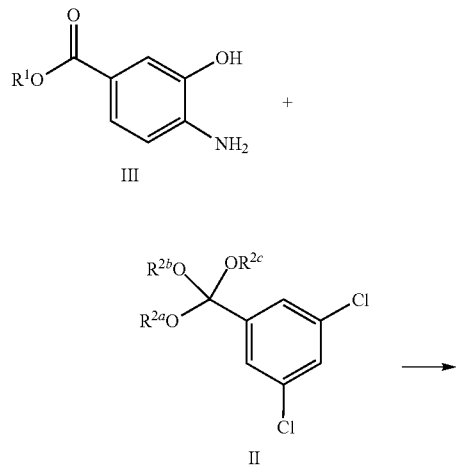

-continued

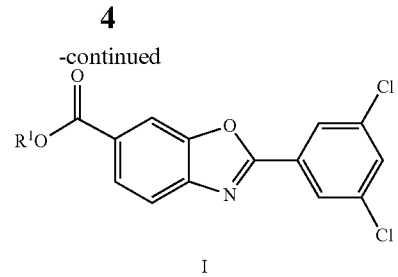

I wherein R¹ is hydrogen or a carboxy protecting group; and R²ᵃ, R²ᵇ and R²ᶜ are each independently $C_1$-$C_6$alkyl or any two of R²ᵃ, R²ᵇ and R²ᶜ taken together are a $C_1$-$C_6$alkanediyl or R²ᵃ, R²ᵇ and R²ᶜ taken together are a $C_3$-$C_{10}$alkanetriyl.

Additional embodiments of the present invention are described hereinafter as embodiments 2 to 46 which are designated as E2 to E46, respectively.

E2 is the process of E1 wherein the reaction of the compound of Formula III with the compound of Formula II to provide the compound of Formula I is carried out in a solvent.

E3 is the process of E2 wherein the solvent is selected from the group consisting of methanol, ethanol, isopropanol, n-butanol, acetone, methyl ethyl ketone, tetrahydrofuran, 1,4-dioxane, t-butyl methyl ether, anisole, ethyl acetate, chloroform, chlorobenzene, heptane, cyclohexane, toluene, acetonitrile and 1,2-dimethoxyethane.

E4 is the process of E3 wherein the solvent is selected from the group consisting of methanol, isopropanol, acetonitrile, ethyl acetate, 1,2-dimethoxyethane, tetrahydrofuran, t-butyl methyl ether and 1,4-dioxane.

E5 is the process of any one of E1 to E4 wherein the reaction of the compound of Formula III with the compound of Formula II to provide the compound of Formula I is carried out in the presence of an acid catalyst.

E6 is the process of E5 wherein the acid catalyst is selected from the group consisting of trifluoroacetic acid, acetic acid, hydrochloric acid and methanesulfonic acid.

E7 is the process of any one of E1 to E4 wherein the reaction of the compound of Formula III with the compound of Formula II to provide the compound of Formula I is carried out in the presence of a base catalyst.

E8 is the process of E7 wherein the base catalyst is triethylamine.

E9 is the process of any one of E1 to E8 wherein the reaction of the compound of Formula III with the compound of Formula II to provide the compound of Formula I is carried out at a temperature of about room temperature to about 100° C.

E10 is the process of E9 wherein the temperature is about room temperature to about 65° C.

E11 is the process of any one of claims E1 to E10 wherein the reaction of the compound of Formula III with the compound of Formula II to provide the compound of Formula I is carried out for a period of about 0.25 hours to about 40 hours.

E12 is the process of any one of E1 to E11 wherein R¹ is hydrogen.

E13 is the process of any one of E1 to E12 wherein R²ᵃ, R²ᵇ and R²ᶜ are each independently $C_1$-$C_6$alkyl.

E14 is the process of E13 wherein R²ᵃ, R²ᵇ and R²ᶜ are each methyl.

E15 is the process of any one of E1 to E12 wherein R²ᵃ, R²ᵇ and R²ᶜ taken together are a $C_3$-$C_{10}$alkanetriyl.

E16 is the process of E15 wherein the compound of Formula II is

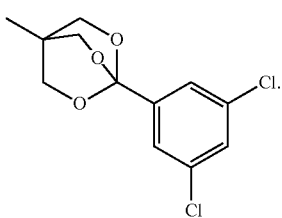

E17 is the process of any one of E1 to E16 further comprising the step of isolating the compound of Formula I.

E18 is the process of E17 wherein the compound of Formula I is isolated by filtration.

E19 is a process for preparing 6-Carboxy-2-(3,5-dichlorophenyl)benzoxazole of Formula Ia

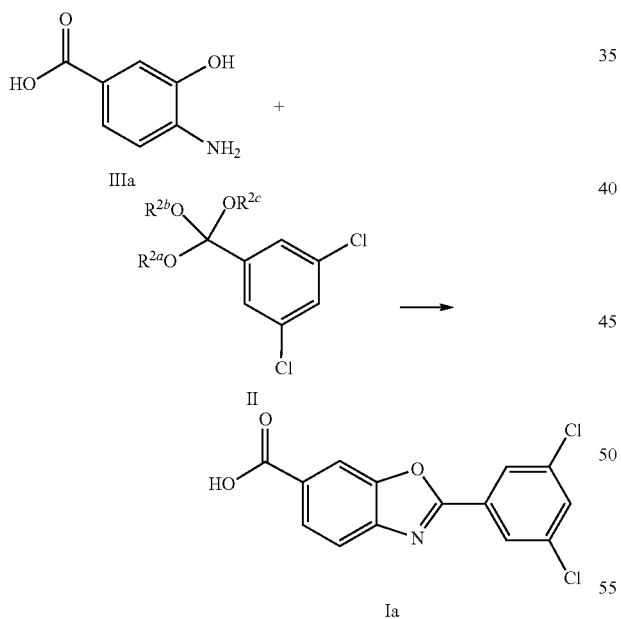

the process comprising reacting 4-Amino-3-hydroxybenzoic acid of Formula IIIa with a 3,5-Dichlorophenyl ortho ester compound of Formula II to provide 6-Carboxy-2-(3,5-dichlorophenyl)benzoxazole of Formula Ia wherein $R^{2a}$, $R^{2b}$ and $R^{2c}$ are each independently $C_1$-$C_6$alkyl or any two of $R^{2a}$, $R^{2b}$ and $R^{2c}$ taken together are a $C_1$-$C_6$alkanediyl or $R^{2a}$, $R^{2b}$ and $R^{2c}$ taken together are a $C_3$-$C_{10}$alkanetriyl.

E20 is the process of E19 wherein the reaction of the compound of Formula IIIa with the compound of Formula II to provide the compound of Formula Ia is carried out in a solvent.

E21 is the process of E20 wherein the solvent is selected from the group consisting of methanol, ethanol, isopropanol, n-butanol, acetone, methyl ethyl ketone, tetrahydrofuran, 1,4-dioxane, t-butyl methyl ether, anisole, ethyl acetate, chloroform, chlorobenzene, heptane, cyclohexane, toluene, acetonitrile and 1,2-dimethoxyethane.

E22 is the process of E21 wherein the solvent is selected from the group consisting of methanol, isopropanol, acetonitrile, ethyl acetate, 1,2-dimethoxyethane, tetrahydrofuran, t-butyl methyl ether and 1,4-dioxane.

E23 is the process of any one of E19 to E22 wherein the reaction of the compound of Formula IIIa with the compound of Formula II to provide the compound of Formula Ia is carried out in the presence of an acid catalyst.

E24 is the process of E23 wherein the acid catalyst is selected from the group consisting of trifluoroacetic acid, acetic acid, hydrochloric acid and methanesulfonic acid.

E25 is the process of E24 wherein the acid catalyst is trifluoroacetic acid.

E26 is the process of any one of E19 to E22 wherein the reaction of the compound of Formula IIIa with the compound of Formula II to provide the compound of Formula Ia is carried out in the presence of a base catalyst.

E27 is the process of E26 wherein the base catalyst is triethylamine.

E28 is the process of any one of E19 to E27 wherein the reaction of the compound of Formula III with the compound of Formula II to provide the compound of Formula I is carried out at a temperature of about room temperature to about 100° C.

E29 is the process of E28 wherein the temperature is about room temperature to about 65° C.

E30 is the process of any one of E19 to E29 wherein the reaction of the compound of Formula III with the compound of Formula II to provide the compound of Formula I is carried out for a period of about 0.25 hours to about 40 hours.

E31 is the process of any one of E19 to E30 wherein $R^a$, $R^{2b}$ and $R^{2c}$ are each independently $C_1$-$C_6$alkyl.

E32 is the process of E31 wherein $R^{2a}$, $R^{2b}$ and $R^{2c}$ are each methyl.

E33 is the process of any one of E19 to E30 wherein $R^{2a}$, $R^{2b}$ and $R^{2c}$ taken together are a $C_3$-$C_{10}$alkanetriyl.

E34 is the process of E33 wherein the compound of Formula II is

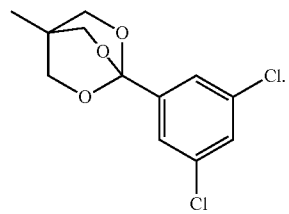

E35 is the process of any one of E19 to E34 further comprising the step of isolating the compound of Formula Ia.

E36 is the process of E35 wherein the compound of Formula Ia is isolated by filtration.

E37 is the process of any one of E19 to E36 further comprising the step of reacting the 6-Carboxy-2-(3,5-dichlorophenyl)benzoxazole of Formula Ia with a pharmaceutically acceptable base to provide a pharmaceutically acceptable salt of 6-Carboxy-2-(3,5-dichlorophenyl)benzoxazole.

E38 is the process of E37 wherein the 6-Carboxy-2-(3,5-dichlorophenyl) benzoxazole is reacted with meglumine in an appropriate solvent to provide 6-Carboxy-2-(3,5-dichlorophenyl)benzoxazole meglumine salt.

E39 is the process of E38 wherein 6-Carboxy-2-(3,5-dichlorophenyl) benzoxazole is reacted at room temperature with meglumine in a solvent selected from methyl isobutyl ketone, MTBE and EtOAc and the resulting solid is isolated and dried to provide the Form E polymorph of 6-Carboxy-2-(3,5-dichlorophenyl)benzoxazole meglumine salt.

E40 is the process of E38 wherein the 6-Carboxy-2-(3,5-dichlorophenyl) benzoxazole is reacted with meglumine in a mixture of IPA and water and the resulting solid is isolated and dried to provide the Form M polymorph of 6-Carboxy-2-(3,5-dichlorophenyl) benzoxazole meglumine salt.

E41 is the process of E35 further comprising the step of stirring the compound of Formula Ia in a mixture of water and IPA then isolating and drying the resulting solid to provide the Form 1 polymorph of 6-Carboxy-2-(3,5-dichlorophenyl)benzoxazole.

E42 is a process for preparing 6-Carboxy-2-(3,5-dichlorophenyl)benzoxazole of Formula Ia

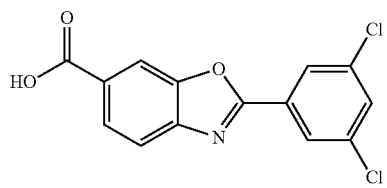

Ia the process comprising reacting about one molar equivalent of 4-Amino-3-hydroxybenzoic acid of Formula IIIa with about one molar equivalent of the 3,5-Dichlorophenyl ortho ester compound of Formula IIa in an appropriate solvent to provide 6-Carboxy-2-(3,5-dichlorophenyl)benzoxazole of Formula Ia

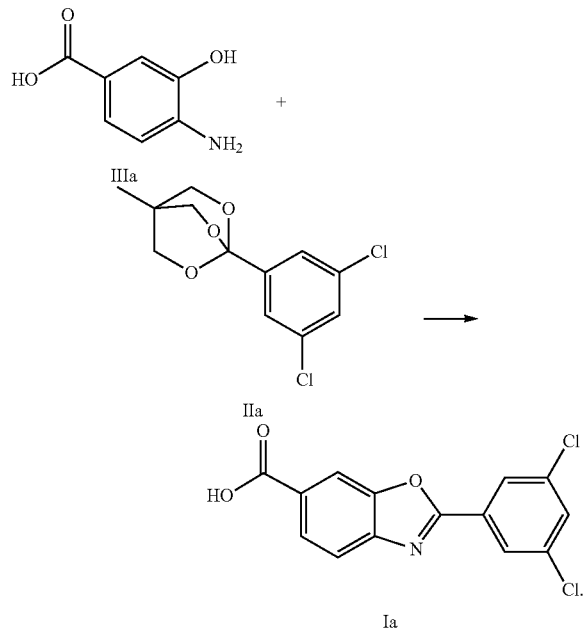

E43 is the process of E42 wherein the solvent is selected from the group consisting of methanol, ethanol, isopropanol, n-butanol, acetone, methyl ethyl ketone, tetrahydrofuran, 1,4-dioxane, t-butyl methyl ether, anisole, ethyl acetate, chloroform, chlorobenzene, heptane, cyclohexane, toluene, acetonitrile and 1,2-dimethoxyethane.

E44 is the process of E43 wherein the solvent is selected from the group consisting of methanol, isopropanol, acetonitrile, ethyl acetate, 1,2-dimethoxyethane, tetrahydrofuran, t-butyl methyl ether and 1,4-dioxane.

E45 is the process of E44 wherein the process is carried out using an acid catalyst selected from the group consisting of trifluoroacetic acid, acetic acid, hydrochloric acid and methanesulfonic acid.

E46 is the process of E44 wherein the acid catalyst is trifluoroacetic acid and the solvent is isopropanol.

E47 is a process for preparing a 6-Carboxy-2-(3,5-dichlorophenyl)benzoxazole compound of Formula I

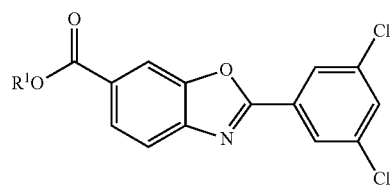

the process comprising reacting a 4-Amino-3-hydroxybenzoic acid compound of Formula III with a 3,5-Dichlorophenyl ortho ester compound of Formula II to provide the compound of Formula I

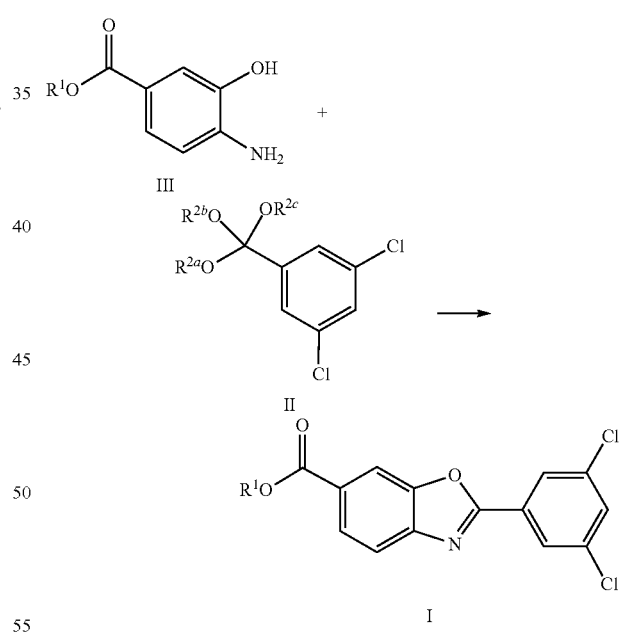

wherein $R^1$ is hydrogen or a carboxy protecting group; and $R^{2a}$, $R^{2b}$ and $R^{2c}$ are each independently $C_1$-$C_6$alkyl or any two of $R^{2a}$, $R^{2b}$ and $R^{2c}$ taken together are a $C_1$-$C_8$alkanediyl or $R^{2a}$, $R^{2b}$ and $R^{2c}$ taken together are a $C_3$-$C_{12}$alkanetriyl, wherein the $C_1$-$C_8$alkanediyl and $C_3$-$C_{12}$alkanetriyl are each optionally substituted with a phenyl which is optionally substituted with one to two groups independently selected from halo, $C_1$-$C_3$alkyl and $C_1$-$C_3$alkoxy.

E48 is the process of E47 wherein the compound of formula III is 4-Amino-3-hydroxybenzoic acid and the compound of formula II is selected from the group consisting of 1,3-Dichloro-5-(trimethoxymethyl)benzene; 1-(3,5-Dichlorophenyl)-4-methyl-2,6,7-trioxabicyclo[2.2.2]octane; 1-(3,5-Dichlorophenyl)-4-ethyl-2,6,7-trioxabicyclo[2.2.2]octane; 1-(3,5-Dichlorophenyl)-4-phenyl-2,6,7-trioxabicyclo[2.2.2]octane; 2-(3,5-Dichlorophenyl)-2-methoxy-1,3-dioxolane; 1-(3,5-Dichlorophenyl)-2,7,8-trioxabicyclo[3.2.1]octane; 3-(3,5-Dichlorophenyl)-2,4,10-trioxaadamantane; 1-(3,5-dichlorophenyl)-4-isopropyl-2,6,7-trioxabicyclo[2.2.2]octane; and 4-(tert-butyl)-1-(3,5-dichlorophenyl)-2,6,7-trioxabicyclo[2.2.2]octane. E49 is the process of E48 wherein the reaction of the compound of Formula II with Formula III is carried out in IPA as solvent in the presence of MSA as acid catalyst.

E50 is a compound selected from the group consisting of 1,3-Dichloro-5-(trimethoxymethyl)benzene; 1-(3,5-Dichlorophenyl)-4-methyl-2,6,7-trioxabicyclo[2.2.2]octane; 1-(3,5-Dichlorophenyl)-4-ethyl-2,6,7-trioxabicyclo[2.2.2]octane; 1-(3,5-Dichlorophenyl)-4-phenyl-2,6,7-trioxabicyclo[2.2.2]octane; 2-(3,5-Dichlorophenyl)-2-methoxy-1,3-dioxolane; 1-(3,5-Dichlorophenyl)-2,7,8-trioxabicyclo[3.2.1]octane; 3-(3,5-Dichlorophenyl)-2,4,10-trioxaadamantane; 1-(3,5-dichlorophenyl)-4-isopropyl-2,6,7-trioxabicyclo[2.2.2]octane; and 4-(tert-butyl)-1-(3,5-dichlorophenyl)-2,6,7-trioxabicyclo[2.2.2]octane.

E51 is the compound of E50 which is 1-(3,5-Dichlorophenyl)-4-methyl-2,6,7-trioxabicyclo[2.2.2]octane. E52 is the compound of E51 which is a crystalline form of 1-(3,5-Dichlorophenyl)-4-methyl-2,6,7-trioxabicyclo[2.2.2]octane. E53 is the compound of E52 which is characterized by PXRD peaks at 21.2 and 19.7 2-theta, each ±0.2 2-theta. E54 is the compound of E53 which is characterized by PXRD peaks at 21.2, 19.7 and 14.4 2-theta, each ±0.2 2-theta. E55 is the compound of E54 which is characterized by PXRD peaks at 21.2, 19.7, 14.4 and 23.7 2-theta, each ±0.2 2-theta. E56 is the compound of E55 which is characterized by PXRD peaks at 21.2, 19.7, 14.4, 23.7 and 24.2 2-theta, each ±0.2 2-theta. E57 is the compound of E56 which is characterized by PXRD peaks at 21.2, 19.7, 14.4, 23.7, 24.2 and 30.6 2-theta, each ±0.2 2-theta.

E58 is a process of preparing a compound of formula IIa-2

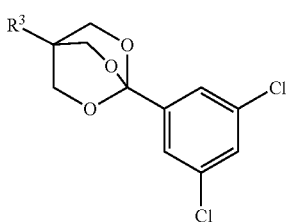

IIa-2 wherein $R^3$ is selected from the group consisting of isopropyl, tert-butyl and neo-pentyl comprising reacting a compound of formula IV with 3,5-dichlorobenzoic acid

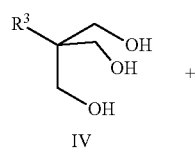

IV

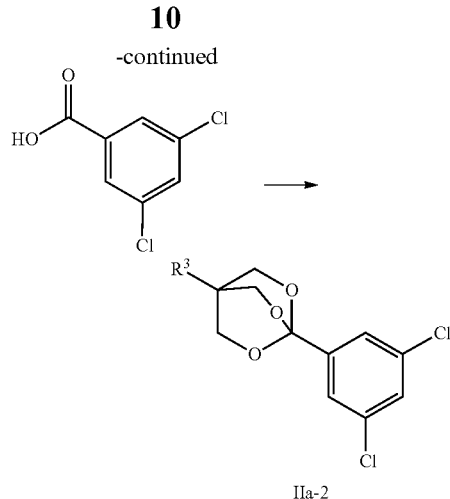

IIa-2 in an appropriate solvent in the presence of an appropriate acid catalyst.

E59 is the process of E58 wherein $R^3$ is isopropyl or tert-butyl. E60 is the process of E59 wherein the solvent is toluene and the acid catalyst is methanesulfonic acid.

In the processes of the present invention described hereinabove the compound of Formula III is either 4-Amino-3-hydroxybenzoic acid (when $R^1$ is H) or a compound wherein the carboxyl group has been protected (when $R^1$ is a carboxyl protecting group). Numerous carboxyl protecting groups are known in the art and can be employed for the compounds of Formula III wherein $R^1$ is a carboxyl protecting group. Chapter 5 of Protective Groups in Organic Synthesis, Third Edition. Theodora W. Greene, Peter G.M. Wuts, Copyright 1999, John Wiley & Sons, Inc. describes various classes of carboxyl protecting groups. Tan J, Akakura M, Yamamoto H. "The supersilyl group as a carboxylic acid protecting group: application to highly stereoselective aldol and Mannich reactions" *Angew Chem Int Ed Engl.* 2013; 52(28):7198-7202. doi:10.1002/anie.201300102 describes the use of supersilyl (EtSi)₃Si— as a versatile carboxyl protecting group. Commonly employed carboxyl protecting groups which can be used for the compound of Formula III include but are not limited to ester protecting groups such as methyl, ethyl, t-butyl, 2-cyanoethyl, 2,2,2-trichloroethyl, allyl, (2,2-dimethyl)allyl, phenyl, benzyl, para-methoxybenzyl and trimethylsilyl in addition to supersilyl. Other equivalent carboxyl protecting groups may also be used, such as use of a thioester (i.e. the $C(O)OR^1$ moiety could instead be $C(O)S(C_1-C_6alkyl)$) or where the entire $C(O)OR^1$ moiety is instead an oxazoline group. The carboxyl protecting groups can be deprotected by methods known in the art, such as by treatment with acid, base or hydrogenation as appropriate for the specific carboxyl protecting group employed to provide compounds wherein $R^1$ is H.

Ortho esters and cyclic orthoester compounds such as those of Formula II used in the instant processes can be prepared according to methods analogous to those as described by E. J. Corey and N. Raju, Tetrahedron Letters, 1983, 24(50), 5571-5574; P. Wipf et. al. Pure Appl. Chem. 1999, 71(3), 415-421; S. Tange et. al. Synthesis, 2008, 3219-3222; M. Noe et. al. Green Chem. 2013, 15, 2252; European Patent Application No. 0279698 and Japanese Patent 5419545 which issued from Japanese Patent Application No. 2010-270091.

Preferred compounds prepared by the process of the invention are compounds of Formula I and more particularly those of Formula Ia, or pharmaceutically acceptable salts thereof. The compound of Formula Ia, 6-Carboxy-1-(3,5-dichlorophenyl)benzoxazole or 2-(3,5-dichlorophenyl)-1,3-benzoxazole-6-carboxylic acid, also known by its USAN name tafamidis, bears a carboxylic acid moiety at the 6-position of its benzoxazole ring. This carboxylic acid moiety can readily form salts with suitable bases, such as meglumine, to provide pharmaceutically acceptable salts of the compounds of Formula Ia.

The processes of this invention include the preparation of compounds of Formula I or Ia in the form of their respective salts derived from inorganic or organic bases. A particular salt of the compound of Formula I or Ia may be advantageous due to one or more of the salt's physical properties, such as enhanced pharmaceutical stability in differing temperatures and humidities, or a desirable solubility in water or oil. In some instances, a salt of a compound also may be used as an aid in the isolation, purification, and/or resolution of the compound in the processes of this invention.

Where a salt is intended to be administered to a patient (as opposed to, for example, being used in an in vitro context), the salt preferably is pharmaceutically acceptable. The term "pharmaceutically acceptable salt" refers to a salt prepared by combining a compound of Formula I or Ia with a base whose cation, is generally considered suitable for human consumption. Pharmaceutically acceptable salts are particularly useful as products of the processes of the present invention because of their greater aqueous solubility relative to the parent compound. For use in medicine, the salts of the compounds prepared by the processes of this invention are non-toxic "pharmaceutically acceptable salts." Salts encompassed within the term "pharmaceutically acceptable salts" refer to non-toxic salts of the compounds of this invention which are generally prepared by reacting the free acid of the compound of Formula I or Ia with a suitable organic or inorganic base.

Since the compounds prepared by the processes of the invention can carry an acidic moiety (i.e. Formula I wherein $R^1$ is H), suitable pharmaceutically acceptable salts thereof may include the lighter alkali metal salts, i.e., sodium or potassium salts; alkaline earth metal salts, e.g., calcium or magnesium salts; and salts formed with suitable organic ligands, e.g., quaternary ammonium salts. In another embodiment, base salts are formed from bases which form non-toxic salts, including aluminum, arginine, benzathine, choline, diethylamine, diolamine, glycine, lysine, meglumine, olamine, tromethamine and zinc salts.

Organic salts may be made from secondary, tertiary or quaternary amines, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups may be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibutyl, and diamyl sulfates), long-chain halides (e.g., decyl, lauryl, myristyl, and stearyl chlorides, bromides, and iodides), arylalkyl halides (e.g., benzyl and phenethyl bromides), and others. A preferred salt prepared by the processes of the present invention is the meglumine salt of tafamidis.

Hemisalts of acids (i.e. the compound of Formula I or Ia) may also be formed by the processes of this invention, for example, hemisulfate and hemicalcium salts of tafamidis.

The skilled person will appreciate that the aforementioned salts include ones wherein the counterion is optically active, for example chiral amine bases such as meglumine which is also known as (2R,3R,4R,5S)-6-(Methylamino)hexane-1,2,3,4,5-pentol or N-methyl-D-glucamine.

For a review on suitable salts, see "Handbook of Pharmaceutical Salts: Properties, Selection, and Use" by Stahl and Wermuth (Wiley-VCH, Weinheim, Germany, 2002).

The pharmaceutically acceptable salts of compounds of Formulae I and Ia may be prepared by one or more of three methods:
(i) by reacting the compound of Formula I or Ia with the desired base;
(ii) by removing a base-labile protecting group from a suitable precursor of the compound of Formula I or Ia using the desired base; or
(iii) by converting one salt of the compound of Formula I or Ia to another by reaction with an appropriate base or by means of a suitable ion exchange column.

All three reactions are typically carried out in solution. The resulting salt may precipitate out and be collected by filtration or may be recovered by evaporation of the solvent. The degree of ionization in the resulting salt may vary from completely ionized to almost non-ionized. A preferred salt of tafamidis which can be prepared is tafamidis meglumine.

The compounds of Formula I or pharmaceutically acceptable salts thereof prepared by the processes of this invention may exist in both unsolvated and solvated forms. The term 'solvate' is used herein to describe a molecular complex comprising a compound of Formula I or a pharmaceutically acceptable salt thereof and one or more pharmaceutically acceptable solvent molecules, for example, ethanol. The term 'hydrate' is employed when said solvent is water. Pharmaceutically acceptable solvates in accordance with the invention include those wherein the solvent of crystallization may be isotopically substituted, e.g. $D_2O$, $d_6$-acetone and $d_6$-DMSO.

A currently accepted classification system for organic hydrates is one that defines isolated site, channel, or metal-ion coordinated hydrates—see *Polymorphism in Pharmaceutical Solids* by K. R. Morris (Ed. H. G. Brittain, Marcel Dekker, 1995), incorporated herein by reference. Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

Also included within the scope of the invention are processes for preparing multi-component complexes (other than salts and solvates) of compounds of Formula I or pharmaceutically acceptable salts thereof wherein the drug (i.e. compound of Formula I or Ia (tafamidis)) and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals containing the compound of Formula I may be prepared by melt crystallisation, by recrystallisation from solvents, or by physically grinding the components together—see Chem Commun, 17, 1889-1896, by O. Almarsson and M. J. Zaworotko (2004), incorporated herein by reference. For a general review of multi-component complexes, see J Pharm Sci, 64 (8), 1269-1288, by Haleblian (August 1975), incorporated herein by reference.

The compounds prepared by the processes of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterized by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ('melting point'). Preferred forms of the compound of Formula Ia, tafamidis (free acid), prepared by the processes of this invention, include the polymorphic forms as described in U.S. Pat. No. 9,770,441 and particularly the Form 1 polymorph of tafamidis free acid as described therein. Preferred forms of the compound of Formula Ia, tafamidis meglumine (the meglumine salt of tafamidis) prepared by the processes of this invention include the polymorphic forms of tafamidis meglumine as described in U.S. Pat. No. 9,249,112 and U.S. Patent Application Publication No. US 2019/0119226. A particularly preferred form of tafamidis meglumine prepared by the processes of this invention is the Form M polymorph as described in U.S. Pat. No. 9,249,112. Another form of tafamidis meglumine that can be prepared using the processes of the present invention is the Form E polymorph of tafamidis meglumine as described in U.S. Patent Application Publication No. US 2019/0119226.

The compounds of Formula I or Ia prepared by the process of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as —COO$^-$Na$^+$, —COO$^-$K$^+$, or —COO$^-$meglumine$^+$) polar head group as is the case with tafamidis. For more information, see *Crystals and the Polarizing Microscope* by N. H. Hartshorne and A. Stuart, 4$^{th}$ Edition (Edward Arnold, 1970), incorporated herein by reference.

ABBREVIATIONS

The following abbreviations were used:
AcOH=acetic acid
AHBA=4-Amino-3-hydroxybenzoic acid
BF$_3$.Et$_2$O=boron trifluoride etherate
13C=carbon 13
° C.=degrees Celsius
CDCl$_3$=deutero chloroform
cm$^{-1}$=reciprocal centimeter
d=doublet
dd=doublet of doublets
DCM=dichloromethane
1,2-DME=1,2-dimethoxyethane
DMSO-d$_6$=deutero dimethylsulfoxide
EtOAc=ethyl acetate
EtOH=ethanol
eq.=equivalents
g=gram
h=hour
H=hydrogen atom
HCl=hydrochloric acid
HPLC=high pressure liquid chromatography
Hz=hertz
IPA=isopropyl alcohol
iPrOAC=isopropyl acetate
J=coupling constant
KOH=potassium hydroxide
L=liter
m=multiplet
mm=millimeter
M=molar
mbar=millibar
MEK=methyl ethyl ketone
MeOH=methanol
mg=milligram
MHz=megahertz
μL=microliter
mL=milliliter
mmol=millimole
mol=mole
MSA or MSOH=methanesulfonic acid
MTBE=methyl t-butyl ether
NaOMe=sodium methoxide
n-BuOH=n-butanol
NMR=nuclear magnetic resonance
PTSA=para-toluene sulfonic acid
RT=room temperature
s=singlet
t=triplet
TEA=triethylamine
THF=tetrahydrofuran
TFA=trifluoroacetic acid

PREPARATIONS

Preparation 1:
1,3-Dichloro-5-(trimethoxymethyl)benzene 1,3-Dichloro-5-(trimethoxymethyl)benzene was prepared according to the method depicted in Reaction Scheme P1 and as described below.

Reaction Scheme P1

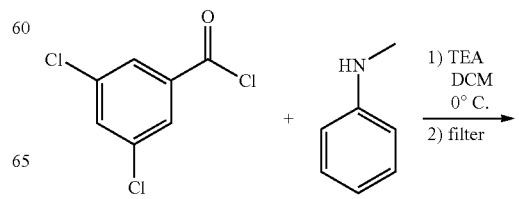

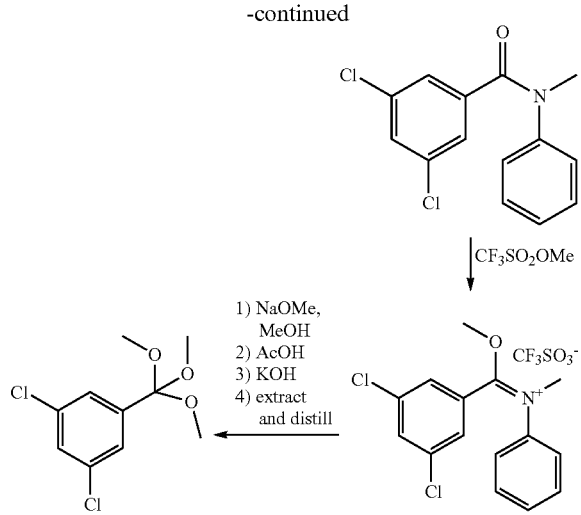

Step 1: Preparation of (E)-[(3,5-dichlorophenyl)-methoxy-methylene]-methyl-phenylammonium; trifluromethane sulfonate To a stirred solution of N-methylaniline (150 g, 1399.9 mmol) in DCM (1200 mL, 1590 g) was added TEA (141.7 g, 1400 mmol) and the resulting solution was cooled to 0° C. over a period of 30 minutes. To this solution was added a solution of 3,5-dichlorobenzoyl chloride (308 g, 1470.4 mmol, 1.05 eq.) in DCM (300 mL, 398 g) over a period of 60 minutes while maintaining the temperature at <5° C. The reaction mixture was stirred for 30 minutes at 0° C. then filtered to remove triethylamine hydrochloride. The resulting filtrate was cooled to 0° C. and to it was added methyl trifluoromethane sulfonate (288.3 g, 1687 mmol, 1.205 eq.) over a period of 60 minutes. The reaction mixture was heated to 52° C. and stirred for 12 h then was concentrated by distillation to a volume of 900 mL. The mixture was cooled to 20° C. over a period of 20 minutes and to it was added MTBE (1500 mL, 1113 g) over a period of 60 minutes. The mixture was cooled to 0° C. over a period of 30 minutes and stirred at 0° C. for 30 minutes. The reaction mixture was filtered and the filter cake was washed with MTBE (300 mL, 223 g). The resulting solid was dried overnight under vacuum to provide 450 g of (E)-[(3,5-dichlorophenyl)-methoxy-methylene]-methyl-phenylammonium; trifluromethane sulfonate (72% yield).

Step 2: Preparation of 1,3-dichloro-5-(trimethoxymethyl)benzene

To a solution of sodium methoxide in methanol (25 weight % in methanol, 364.9 g, 386.1 mL, 1520 mmol, 1.5 eq.) at 0° C. was added a solution of (E)-[(3,5-dichlorophenyl)-methoxy-methylene]-methyl-phenyl-ammonium; trifluoromethane sulfonate (450 g, 1013 mmol) in MeOH (3000 mL) over a period of 60 minutes while maintaining the temperature at <5° C. The reaction mixture was stirred for 30 minutes then to it was added AcOH (206.4 mL, 216.3 g, 3.2 eq.) over a period of 30 minutes while maintaining the temperature at <5° C. This reaction mixture was then added over a period of 60 minutes to a reactor containing 4M aqueous potassium hydroxide (1317 g, 1126 mL, 4 eq.) while maintaining the temperature at 20° C. The reaction mixture was then heated and concentrated by distillation to a volume of 1500 mL. The reaction mixture was adjusted to 20° C. and to it was added water (1250 mL) and DCM (1250 mL). Agitation of the mixture was halted and the layers were allowed to separate and then the lower organic layer was collected. To the remaining aqueous layer was added DCM (1250 mL) and the mixture was agitated for 10 minutes, the agitation was halted and the layers allowed to separate and the lower organic layer was collected. The combined organic layers were then distilled, first under atmospheric pressure with the fraction boiling up to 100° C. being discarded, followed by vacuum distillation at 5-10 mbar while increasing the reactor temperature from 95° C. to 160° C. over a period of 2 h. The desired orthoester, 1,3-dichloro-5-(trimethoxymethyl)benzene was collected as a pale yellow oil (201.9 g, 803.4 mmol, 79.3% yield). 1H NMR (500 MHz, CDCl$_3$) δ 7.48 (d, J=1.9 Hz, 2H), 7.36 (t, J=1.9 Hz, 1H), 3.15 (s, 9H). 13C NMR (126 MHz, CDCl$_3$) δ 140.4, 134.9, 129.0, 126.2, 113.7, 49.9. FTIR (neat): 1568.2, 1418.8, 1256.3, 1094.5, 987.2, 862.7, 796.0, 656.6, 517.3 cm$^{-1}$.

Preparation 2: 1-(3,5-dichlorophenyl)-4-methyl-2,6,7-trioxabicyclo[2.2.2]octane 1-(3,5-dichlorophenyl)-4-methyl-2,6,7-trioxabicyclo[2.2.2]octane was prepared according to the method depicted in Reaction Scheme P2 and as described below.

Reaction Scheme P2

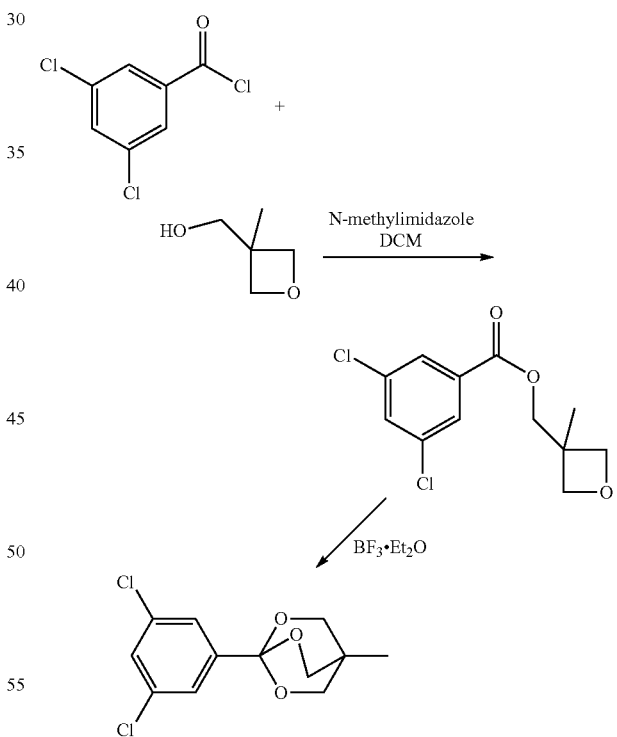

Step 1: Synthesis of (3-methyloxetan-3-yl)methyl 3,5-dichlorobenzoate

To a solution of 3-methyl-3-oxetanemethanol (54.3 g, 0.53 mol) in DCM (400 mL) at ~0° C. was added a solution of 3,5-dichlorobenzoyl chloride (111.4 g, 0.53 mol) in DCM (100 mL) over a period of 45 minutes. The mixture was stirred at ~0° C. for 1.5 h then was washed with water (3×200 mL). The organic layer was then concentrated to remove DCM. This resulted in 143.7 g (98.6% crude yield) of a colorless viscous oil which crystallized on standing. Half of this material was carried on to the next step while the other half of this material was recrystallized from IPA (250 mL) to provide 55.0 g of (3-methyloxetan-3-yl)methyl 3,5-dichlorobenzoate as a colorless crystalline solid. 1H NMR (44 MHz, CDCl$_3$) d 7.85 (d, 2H), 7.55 (t, 1H), 4.75-4.28 (m, 6H), 1.45 (s, 3H).

Step 2: Synthesis of 1-(3,5-dichlorophenyl)-4-methyl-2, 6, 7-trioxabicyclo[2.2.2]octane A solution of (3-methyloxetan-3-yl)methyl 3,5-dichlorobenzoate (71.85 g, 0.261 mol) in DCM (435 mL) was cooled to −5° C. in an acetone/ice bath. To this solution was added boron trifluoride etherate (BF$_3$.Et$_2$O, 9.4 g, 66.25 mmol) and the solution was stirred overnight while warming to RT to provide a yellow solution. To this solution was added TEA (25.0 g, 0.247 mol) and the mixture was stirred for 1 h at RT then to it was added MTBE (520 mL). As no precipitate formed the mixture was concentrated to remove the solvent which resulted in an orange yellow solid (crude weight ~85 g) which was recrystallized in IPA (250 mL) to provide 41.6 g (57% yield) of the desired product. A further two crops were obtained by concentrating the mother liquor and seeding with material from the 1$^{st}$ crop to provide an additional 5.0 g and 3.46 g, respectively, of the desired product 1-(3,5-dichlorophenyl)-4-methyl-2, 6, 7-trioxabicyclo[2.2.2]octane. Total yield obtained was 50.06 g (68%).

HPLC retention time 5.062 minutes; 1H NMR (44 MHz, CDCl$_3$) δ 7.83-7.13 (m, 3H), 4.15 (s, 6H), 0.97 (s, 3H).

Crystalline 1-(3,5-dichlorophenyl)-4-methyl-2, 6, 7-trioxabicyclo[2.2.2]octane was evaluated using PXRD and the peak picked spectrum is provided as FIG. 1. The 2-theta values are provided in PXRD Table 1, below, and are ±0.2 2-theta. The crystalline form of 1-(3,5-dichlorophenyl)-4-methyl-2,6,7-trioxabicyclo[2.2.2]octane is characterized by PXRD peaks at 21.2 and 19.7 2-theta, each ±0.2 2-theta; 21.2, 19.7 and 14.4 2-theta, each ±0.2 2-theta; 21.2, 19.7, 14.4 and 23.7 2-theta, each ±0.2 2-theta; 21.2, 19.7, 14.4, 23.7 and 24.2 2-theta, each ±0.2 2-theta; 21.2, 19.7, 14.4, 23.7, 24.2 and 30.6 2-theta, each ±0.2 2-theta.

TABLE 1

| | PXRD | | |
|---|---|---|---|
| Index | Angle(2-theta) | d Value | Rel. Intensity |
| 1 | 11.30 | 7.824108 | 0.007597719 |
| 2 | 12.12 | 7.298122 | 0.01661962 |
| 3 | 14.38 | 6.156159 | 0.7438484 |
| 4 | 15.55 | 5.691941 | 0.1679692 |
| 5 | 16.21 | 5.462939 | 0.009178909 |
| 6 | 17.53 | 5.054135 | 0.2085875 |
| 7 | 17.95 | 4.936231 | 0.3470413 |
| 8 | 18.52 | 4.785399 | 0.2930813 |
| 9 | 19.68 | 4.506914 | 0.8610104 |
| 10 | 20.10 | 4.413914 | 0.1670985 |
| 11 | 21.16 | 4.19524 | 1 |
| 12 | 22.50 | 3.94742 | 0.1139737 |
| 13 | 23.72 | 3.747795 | 0.6063656 |
| 14 | 24.21 | 3.673261 | 0.3798759 |
| 15 | 25.12 | 3.542264 | 0.1981285 |
| 16 | 25.58 | 3.479031 | 0.09517884 |
| 17 | 26.33 | 3.38264 | 0.0418138 |
| 18 | 27.13 | 3.283952 | 0.02625476 |
| 19 | 28.04 | 3.179178 | 0.1545492 |

TABLE 1-continued

| | PXRD | | |
|---|---|---|---|
| Index | Angle(2-theta) | d Value | Rel. Intensity |
| 20 | 28.83 | 3.094686 | 0.2470139 |
| 21 | 29.22 | 3.053421 | 0.07650879 |
| 22 | 29.55 | 3.020665 | 0.02373517 |
| 23 | 29.92 | 2.983938 | 0.01153463 |
| 24 | 30.38 | 2.93984 | 0.08511703 |
| 25 | 30.64 | 2.91577 | 0.3058709 |
| 26 | 31.24 | 2.85998 | 0.1483398 |
| 27 | 32.26 | 2.772916 | 0.04282971 |
| 28 | 32.52 | 2.750854 | 0.1430239 |
| 29 | 33.67 | 2.660037 | 0.03918915 |
| 30 | 33.82 | 2.648182 | 0.1131594 |
| 31 | 34.22 | 2.618398 | 0.124439 |
| 32 | 34.79 | 2.576881 | 0.07517909 |
| 33 | 35.17 | 2.549943 | 0.04215604 |
| 34 | 36.20 | 2.479342 | 0.02800754 |
| 35 | 37.13 | 2.419532 | 0.05378346 |
| 36 | 37.43 | 2.400943 | 0.1851316 |
| 37 | 37.91 | 2.371541 | 0.02901557 |
| 38 | 38.56 | 2.3327 | 0.03799857 |
| 39 | 39.51 | 2.27912 | 0.02013857 |
| 40 | 40.42 | 2.229635 | 0.03245644 |
| 41 | 40.68 | 2.215911 | 0.09965967 |
| 42 | 41.50 | 2.174133 | 0.04171338 |
| 43 | 42.11 | 2.143933 | 0.01916863 |
| 44 | 42.56 | 2.122431 | 0.01784119 |
| 45 | 42.81 | 2.110647 | 0.07835057 |
| 46 | 43.42 | 2.082178 | 0.04826967 |
| 47 | 43.75 | 2.067322 | 0.2739744 |
| 48 | 44.23 | 2.04628 | 0.1211933 |
| 49 | 44.74 | 2.023906 | 0.128445 |
| 50 | 45.08 | 2.009188 | 0.03454069 |
| 51 | 45.76 | 1.98109 | 0.06844667 |
| 52 | 46.63 | 1.946051 | 0.02381395 |
| 53 | 47.03 | 1.930426 | 0.03673584 |
| 54 | 47.88 | 1.898281 | 0.03710467 |
| 55 | 48.42 | 1.878401 | 0.0482191 |
| 56 | 48.80 | 1.864614 | 0.06447587 |
| 57 | 49.31 | 1.846388 | 0.04025196 |
| 58 | 50.39 | 1.809317 | 0.04403515 |
| 59 | 51.32 | 1.778826 | 0.06215513 |
| 60 | 52.41 | 1.744433 | 0.04581038 |
| 61 | 53.26 | 1.718503 | 0.00936179 |
| 62 | 53.95 | 1.698118 | 0.007044924 |

Preparation 3: 1-(3,5-Dichlorophenyl)-4-ethyl-2,6,7-trioxabicyclo[2.2.2]octane

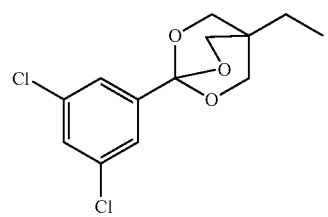 [SMILES: CCC12COC(c3cc(Cl)cc(Cl)c3)(OC1)OC2]

To a solution of 1,3-dichloro-5-(trimethoxymethyl)benzene (10.04 g, 40.0 mmol) in anhydrous DCM (40 mL) was added 2-ethyl-2-(hydroxymethyl)-1,3-propanediol (5.375 g, 40.0 mmol) followed by TFA (0.3 mL, 3.9 mmol) and the mixture was stirred at room temperature for 65 h. Anhydrous K$_2$CO$_3$ (2.2 g) was added, the mixture was agitated for 3 h, then filtered. The filtrate was concentrated on a rotary evaporator and the residue was dissolved in hot toluene (70 mL), cooled to rt and filtered through PTFE membrane then concentrated in vacuo to provide a residue (12.40 g) that solidified. The residue was crystallized from heptanes:heptane (50 mL) was added, the solid was dissolved under reflux and the solution was then kept at −5° C. for 3 h. Solid precipitate was filtered off, rinsed with chilled heptanes and air dried; this afforded a first crop of crude product (6.12 g). The combined filtrate was evaporated to half the original volume then left at −5° C. overnight; a second crop (1.45 g) of the substance was collected by filtration. Both portions contained the desired 2,6,7-trioxabicyclo[2.2.2]octane admixed with a by-product, 2,2-bis(hydroxymethyl)butyl 3,5-dichlorobenzoate. The first crop in molar ratio of desired product:by-product of 1:0.25, and the second crop in ratio of 1:0.37.

Both portions of crude material obtained were combined with another batch that had been prepared in a similar manner (7.58 g, desired product:by-product ratio 1:0.18).

The combined crude product (15.15 g) was re-crystallized from i-PrOAc (35 mL). The solid was dissolved under heating below reflux temperature and the solution was then left at room temperature for 2 h. Precipitated solid was filtered off, rinsed with cold i-PrOAc and air dried; so, material having product/by-product ratio 1:5.2 was obtained (0.77 g).

The filtrate was left at −5° C. overnight, the precipitated solid was separated and the filtrate stepwise evaporated/cooled. These manipulations gave four batches of the product of insufficient purity. They were combined in one batch (11.02 g, product/by-product ratio 1:0.11) and crystallized repeatedly: the batch was dissolved in i-PrOAc (25 mL) kept at rt for 1 h then cooled to −5° C. and subjected to brief sonification. This caused spontaneous crystallization. Immediate filtration afforded crystalline product in 2.46 g amount after vacuum drying, batch 1, assay 97.4% (qNMR).

The filtrate afforded many crystalline crops of insufficient quality; the crystalline crops were then re-combined.

Collected raw material (8.50 g) was re-crystallized from isopropanol: the sample was dissolved in 45 mL of i-PrOH by heating, additional 45 mL volume of i-PrOH were added, the solution was cooled to rt and kept at this temperature for 1 h then put in refrigerator at −5° C. for 10 min. The first crystals appeared in this time. Further the solution was kept at 0° C. for 1 h then crystalline substance was collected by filtration, rinsed with cooled i-PrOH and dried under vacuum. The title compound was obtained in 6.67 g amount, batch 2, assay 95.4% (qNMR).

The filtrate was evaporated to half its original volume and left at 0° C. overnight. The next crop of crystals was collected by filtration and rinsed with cooled i-PrOH and dried under vacuum. Target substance was obtained in 1.81 g amount, batch 3, assay 97.2% (qNMR).

For Batches 1-3: each batch had m.p. 76° C.; each batch had $^1$H NMR and $^{13}$C NMR as follows:

$^1$H NMR (400 MHz, CDCl$_3$), δ, ppm: 7.52 (d J=2.0 Hz, 2H), 7.33 (t J=2.0 Hz, 1H), 4.09 (s, 6H), 1.32 (q J=7.7 Hz, 2H), 0.88 (t J=7.7 Hz).

$^{13}$C NMR (101 MHz, CDCl$_3$), δ, ppm: 140.7, 134.8, 129.3, 124.9, 106.7, 72.0, 33.7, 22.5, 7.7.

HRMS: ES+ m/z,(%): calculated for C$_{13}$H$_{15}$Cl$_2$O$_3$ [M+1]+289.0398; Batch 1 found 289.0410; Batch 2 found 289.0407; and Batch 3 found 289.0404.

Preparation 4: 1-(3,5-Dichlorophenyl)-4-phenyl-2,6,7-trioxabicyclo[2.2.2]octane

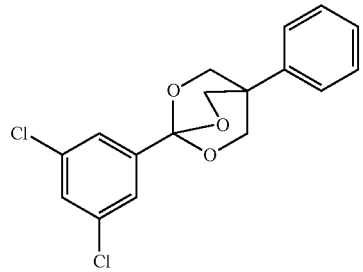 [SMILES: Clc1cc(Cl)cc(C23OCC(c4ccccc4)(CO2)CO3)c1]

Step 1: Preparation of 1,1,1-Tris(hydroxymethyl)phenylmethane

Phenylacetaldehyde (12.4 mL, 0.11 mol) and Ca(OH)$_2$ (31.5 g, 0.43 mol) were added to a suspension of paraformaldehyde (12.8 g, 0.43 mol) in anhydrous THF (160 mL). The reaction mixture was stirred at 60-65° C. (bath temperature) for 4 days.

After cooling to room temperature the reaction mixture was filtered through Celite, and the filter pad was rinsed with DCM. The combined filtrates were concentrated on a rotary evaporator. The residual oil was treated with ethyl acetate, seeded (with solid from previous experiments, isolated by chromatography) and left in refrigerator overnight. Crystalline solid formed was collected by filtration and washed with chilled EtOAc, and dried to provide the target triol compound (9.8 g, 49% yield).

Step 2: Preparation of 1-(3,5-Dichlorophenyl)-4-phenyl-2,6,7-trioxabicyclo[2.2.2]octane To 1,3-dichloro-5-(trimethoxymethyl)benzene (6.3 g, 0.025 mol) and 1,1,1-Tris(hydroxymethyl)phenylmethane (4.6 g, 0.025 mol) suspended in anhydrous DCM (40 mL) was added 0.19 mL (0.0025 mol) of TFA. The suspension became a clear solution and it was left at room temperature for 48 h then K$_2$CO$_3$ was added and the mixture was agitated for 3 h. The mixture was filtered and solvent evaporated. An attempt to dissolve the residue (~9 g) in boiling toluene (25 mL) led to incomplete dissolution. After cooling to ambient temperature the solution was decanted and cooled. The resulting solid that formed was collected by filtration and crystallized from n-heptane to obtain white soft substance (5.2 g).

Another experiment carried out at the same scale gave 5.0 g of the product.

The combined batches were crystallized from isopropyl acetate to provide 5.78 g of 2,6,7-trioxabicyclo[2.2.2]octane; Batch 1, assay 99.6% (qNMR); The filtrate from Batch 1 was cooled and stored at 0° C. overnight. An additional 1.85 g of 2,6,7-trioxabicyclo[2.2.2]octane was then collected by filtration. Batch 2, assay 98.0% (qNMR). Total yield of the re-crystallized product was 45%.

Batch 1 had m.p. of 139° C.; Batch 2 had m.p. of 138° C. Batch 1 and Batch 2 each had $^1$H NMR (400 MHz, CDCl$_3$), δ, ppm: 7.59 (d J=2.0 Hz, 2H), 7.39-7.45 (m, 2H), 7.33, 7.39 (m, 2H), 7.17-7.23 (m, 2H), 4.15 (s, 6H).

$^{13}$C NMR spectrum (101 MHz, CDCl$_3$), δ, ppm: 140.4, 135.6, 134.9, 129.5, 129.4, 128.4, 125.4, 125.0, 107.2, 72.4, 37.1.

HRMS ES+m/z,(%): calculated for C$_{17}$H$_{15}$Cl$_2$O$_3$ [M+1]+ 337.0398; found 337.0406.

Preparation 5:
2-(3,5-Dichlorophenyl)-2-methoxy-1,3-dioxolane

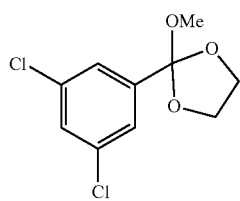 [SMILES: COC1(c2cc(Cl)cc(Cl)c2)OCCO1]

To a solution of 1,3-dichloro-5-(trimethoxymethyl)benzene (10.04 g, 40.0 mmol) in anhydrous DCM (40 mL) was added ethylene glycol (2.7 mL, 48.3 mmol, 1.2 eq) followed by TFA (0.3 mL, 3.9 mmol) and the mixture was stirred at room temperature for 72 h. Anhydrous K$_2$CO$_3$ (1.5 g) was added, the mixture was stirred for 2 h, then filtered. The filtrate was evaporated to dryness and resulted in a yellow oil (10.76 g). The obtained oil was subjected to vacuum distillation, collecting fraction boiling at 160-185° C./16 mbar. The collected fraction (turbid greenish oil) was further purified by repeated distillation collecting distillate at 180-183° C./16 mbar. Distillation afforded the desired product (5.63 g) as a yellow oil, assay 96.2% (qNMR).

$^1$H NMR spectrum (400 MHz, CDCl$_3$), δ, ppm: 7.47 (d J=1.9 Hz, 2H), 7.34 (t, J=1.9 Hz, 1H), 4.19-4.30 (m, 2H), 4.03-4.13 (m, 2H), 3.28 (s, 3H).

$^{13}$C NMR spectrum (101 MHz, CDCl$_3$), δ, ppm: 141.4, 135.0, 129.1, 125.0, 120.1, 65.6, 50.4.

GCMS m/z,(%): 217 (100) [M-OMe]+, 173 (71) [C$_7$H$_3$Cl$_2$O]+, 145 (30) [C$_6$H$_3$C$_{12}$]+

Preparation 6: 1-(3,5-Dichlorophenyl)-2,7,8-trioxabicyclo[3.2.1]octane

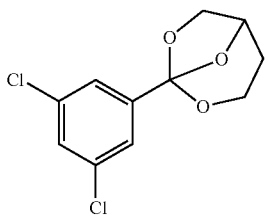 [SMILES: Clc1cc(Cl)cc(C23OCCC(CO2)O3)c1]

To a solution of 1,3-dichloro-5-(trimethoxymethyl)benzene (10.04 g, 40.0 mmol) in anhydrous DCM (50 mL) was added 1,2,4-butanetriol (3.57 mL, 40.0 mmol) followed by addition of TFA (0.3 mL, 3.9 mmol) and the mixture was stirred at room temperature for 18 h. Anhydrous K$_2$CO$_3$ (1.5 g) was added, the mixture was stirred for 2 h, then filtered. The filtrate evaporated till dryness gave yellow oil (10.6 g) which solidify slowly.

Crude material was dissolved in toluene (30 mL), filtered through PTFE membrane then evaporated under reduced pressure. Heptane (80 mL) was added to the residue, refluxed, then cooled and the upper layer (hexane solution) was decanted. The bottom layer (an oil) was treated with hot heptane repeatedly. Heptane solutions were combined, the volume was reduced till ~25 mL and kept at 4° C. for 3 h. White precipitate was filtered off, rinsed with cold heptane and left to air dry overnight.

Isolated 2,7,8-trioxabicyclo[3.2.1]octane (4.27 g) contained about 11 mol-% of open chain by-products (dihydroxybutyl 3,5-dichlorobenzoates). This product was combined with another sample obtained in a similar manner (4.03 g, contamination by open chain benzoates about 7 mol-%) for further purification.

The combined batch (8.30 g in total) was dissolved in heptane (30 mL) by heating, the solution was filtered hot and kept at room temperature for 5 h. The precipitated solid was collected by filtration and air dried. This afforded 6.78 g of crystalline product. The filtrate was partially evaporated (until about half the original volume) and stored at −5° C. overnight. This gave an additional quantity (second crop) of the solid in 1.03 g amount and a quality similar to that of the main crop. The second crop contained about 6 mol-% of dihydroxybutyl benzoates. Both samples were combined and recrystallized from i-PrOAc as follows. The combined sample (7.84 g) was dissolved in hot isopropyl acetate (10 mL), the solution was cooled, then left at −5° C. overnight. Formed white crystalline substance was collected by filtration, rinsed with cooled i-PrOAc and dried under vacuum at rt to provide the title compound (5.30 g). assay 96.2% (qNMR), m.p. 81-84° C.

$^1$H NMR spectrum (400 MHz, CDCl$_3$), δ, ppm: 7.53 (d J=2.0 Hz, 2H), 7.36 (t J=2.0 Hz, 1H), 4.83 (td J=3.4, 1.6 Hz, 1H), 4.27 (dt J=11.7, 4.2 Hz, 1H), 4.24 (d J=7.2 Hz, 1H), 4.12 (ddd J=7.3, 4.8, 1.6 Hz, 1H), 4.03 (ddd J=11.7, 6.7, 1.0 Hz, 1H), 2.41 (ddddd J=13.8, 12.2, 6.7, 3.4, 1.8 Hz, 1H), 1.51 (dddd J=13.8, 4.2, 2.0, 0.5 Hz, 1H).

$^{13}$C NMR spectrum (101 MHz, CDCl$_3$), δ, ppm: 139.7, 134.9, 129.6, 125.0, 117.2, 73.9, 69.6, 59.5, 28.2.

HRMS ES+m/z,(%): calculated for C$_{11}$H$_{11}$Cl$_2$O$_3$ [M+1]+ 261.0085; found 261.0094.

Preparation 7:
3-(3,5-Dichlorophenyl)-2,4,10-trioxaadamantane

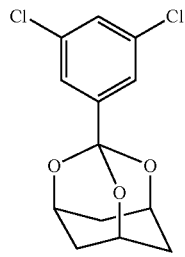 [SMILES: Clc1cc(Cl)cc(C23OC4CC(CC(C4)O2)O3)c1]

To a solution of 1,3-dichloro-5-(trimethoxymethyl)benzene (6.42 g, 25.57 mmol) in anhydrous DCM (50 mL) was added cis-phloroglucitol (2.92 g, 22.16 mmol) followed by dropwise addition of BF$_3$·OEt$_2$ (0.28 mL, 2.21 mmol, ~0.1 eq) to stirred suspension. The mixture was stirred at room temperature for 34 h, then the residual phloroglucitol (0.14 g) was filtered off and the solution was evaporated under reduced pressure. To the residue TBME (40 mL) was added and the mixture was shortly refluxed, complete dissolution was not achieved. The mixture was cooled, kept at 0° C. 1 h then filtered collecting white of precipitate (5.03 g).

Evaporation of the filtrate to a quarter of the original volume gave an additional crop of the solid (0.50 g).

Similar experiment started with 1.61 g (6.41 mmol) of 1,3-dichloro-5-(trimethoxymethyl)-benzene and 0.85 g (6.44 mmol) of cis-phloroglucitol afforded 1.27 g of crude solid.

All solids were combined and dissolved in MEK (30 mL) heating to reflux. The solution was filtered hot and stored overnight at room temperature, then the crystalline solid was filtered off, washed with small volume of cold MEK and dried under vacuum at room temp.; this afforded title compound in 5.586 g amount (yield 61%*), assay 99.8% (qNMR), m.p.188° C.

Filtrate evaporated to ⅓ volumes and stored at −5° C. for 4 h gave additional crop of crystals of the same quality, 0.79 g (yield 9%*), assay 99.8% (qNMR), m.p.188° C.

yield calculated on total amount of starting orthoester in both runs $^1$H NMR (400 MHz, CDCl$_3$), δ, ppm: 7.57 (d, J=1.9 Hz, 2H), 7.33 (t, J=1.9 Hz, 1H), 4.56 (m, 3H), 3.11-2.49 (m, 3H), 1.81 (ddt, J=12.9, 2.1, 1.2 Hz, 2H)

$^{13}$C NMR (101 MHz, CDCl$_3$), δ, ppm: 142.5, 134.8, 129.3, 124.4, 108.1, 69.3, 33.0.

HRMS ES+m/z,(%): calculated for C$_{13}$H$_{13}$Cl$_2$O$_3$ [M+1]$^+$ 287.0242; found 287.0253.

Preparation 8: 1-(3,5-dichlorophenyl)-4-isopropyl-2,6,7-trioxabicyclo[2.2.2]octane

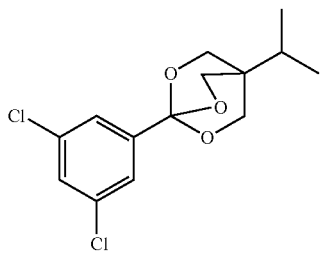 [SMILES: CC(C)C12COC(c3cc(Cl)cc(Cl)c3)(OC1)OC2]

Step 1: Synthesis of 2-isopropyl-2-hydroxymethyl-1,3-propanediol

Isovaleraldehyde (83 g, 1.0 mol) was added over 0.5 h at RT to a solution of sodium hydroxide (60 g, 1.5 mol) in water (1200 mL) containing 37% formaldehyde solution (324 g, 4.0 mol). The solution was then stirred at 50-55° C. for 3 h and allowed stand overnight at RT. It was filtered away from a small amount (2.7 g) of crystalline solid and the solution was weighed (1725 g). Of this, 15% (259 g) was taken and extracted 4× with DCM (200 mL); the extracts were concentrated to afford 7.0 g of oil which crystallized. The resulting solid was shown by 1H NMR to be the ether dimer, namely, (2,2'-(oxybis(methylene))bis(2-isopropyl-propane-1,3-diol)).

The aqueous solution remaining from the preceding DCM extraction was treated with solid sodium chloride (40 g) and extracted with isopropyl acetate (4×200 mL). The combined isopropyl acetate extracts were concentrated in vacuo to afford 14.5 g (97.8 mmol) of the desired 2-isopropyl-2-hydroxymethyl-1,3-propanediol (pure but contains a small amount of isopropyl acetate by 1H NMR).

Step 2: Synthesis of 1-(3,5-dichlorophenyl)-4-isopropyl-2,6,7-trioxabicyclo[2.2.2]octane Toluene (150 mL) was charged, followed by 3,5-dichlorobenzoic acid (DCBA, 17.0 g, 89 mmol) and methanesulfonic acid (MSA, 0.8 g). The mixture was refluxed under Dean-Stark for 6 h; 1.9 g of water was collected (theoretical amount is 3.2 g) and allowed stand overnight The mixture was extracted with 10% KOH solution (100 mL and 20 mL) at 60-70° C., followed by a water wash at the same temperature. Acidification of the aqueous extract, followed by filtration and drying of the resulting white solid gave 8.8 g (53% of the initial) of DCBA.

The toluene solution was concentrated to afford 14.5 of oil, which by NMR contained ca 30% of the desired orthoester. On dissolution in methanol (100 mL) and treatment with solid KOH (5.0 g, 89 mmol), a solution was obtained which deposited crystals on standing. Filtration and washing (methanol) afforded pure 1-(3,5-dichlorophenyl)-4-isopropyl-2,6,7-trioxabicyclo[2.2.2]octane (1.6 g, 13% ex reacted DCBA); $^1$H NMR: δ 7.4 m (2H); 4.0 (s, 6H); 1.4 m (1H) and 0.8 d (6H).

Alternatively, when Step 2 was carried out using paratoluene sulfonic acid (PTSA) as a catalyst rather than MSA there was very poor conversion to the desired ortho ester (90% recovery of DCBA and 30% of theoretical amount of water was generated).

An additional batch of the desired ortho ester was obtained as follows. 388 g of the 1725 g solution (from Step 1 above) was taken (22.5% of the total) and worked up in the same way as described above: 4 extractions with DCM (250 mL) to remove the tetra-ol dimer, followed by addition of NaCl (60 g) and 4 extractions with isopropyl acetate (200 mL) to afford 17.5 g (118.2 mmol) of pure (2-(hydroxymethyl)-2-isopropylpropane-1,3-diol) as a semi-solid. To this semi-solid was charged 3,5-dichlorobenzoic acid (16.5 g, 86.39 mmol), followed by toluene (200 mL) and MSA (1.2 g, 12.5 mmol). The solution was refluxed under Dean-Stark for 6 h, cooled to ambient temperature. There was 2.3 g of water in the trap. Extra MSA (1.2 g) was added and reflux resumed for another 6 h, resulting in an extra 0.5 mL of water. The batch was allowed cool to ambient temperature, treated with 100 mL of 6% KOH solution at 40-50° C., followed by a 100 mL water wash at the same temperature. The toluene was removed to leave 28 g of an oil. This oil was dissolved in methanol (150 mL) and water (10 mL) and treated with potassium hydroxide (6 g, 107 mmol) at ambient temperature (this converts the normal ester to soluble triol and potassium 3,5-dichlorobenzoate). The orthoester then started to crystallize quickly; the suspension was cooled to 0-10° C. for 0.5 h and filtered and washed with methanol and dried to afford 1-(3,5-dichlorophenyl)-4-isopropyl-2,6,7-trioxabicyclo[2.2.2]octane (5.6 g, 21.5%) as a white crystalline powder.

Preparation 9: 4-(tert-butyl)-1-(3,5-dichlorophenyl)-2,6,7-trioxabicyclo[2.2.2]octane

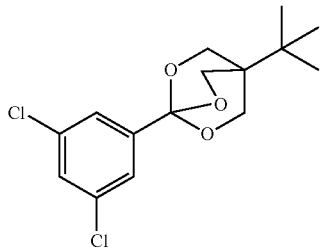 [SMILES: CC(C)(C)C12COC(c3cc(Cl)cc(Cl)c3)(OC1)OC2]

4-(tert-butyl)-1-(3,5-dichlorophenyl)-2,6,7-trioxabicyclo[2.2.2]octane can be prepared in an analogous manner as the compound of Preparation 8 starting from 3,3-dimethylbutanaldehyde (1.0 mol) which is added over 0.5 h at RT to a solution of sodium hydroxide (60 g, 1.5 mol) in water (1200 mL) containing 37% formaldehyde solution (324 g, 4.0 mol). The reaction sequence is then carried out in a manner analogous to Preparation 8 to provide the desired 4-(tert-butyl)-1-(3,5-dichlorophenyl)-2,6,7-trioxabicyclo[2.2.2]octane. In step 2 of the synthesis, in addition to the use of methanesulfonic acid, boron trifluoride etherate may be employed in a similar manner as an alternative acid catalyst.

EXAMPLES

Examples 1-47 were carried out to explore the impact of various parameters as described hereinbelow on the reaction of 4-amino-3-hydroxybenzoic acid with 1,3-dichloro-5-(trimethoxymethyl)benzene to provide 6-carboxy-1-(3,5-dichlorophenyl)benzoxazole (tafamidis) which is depicted below.

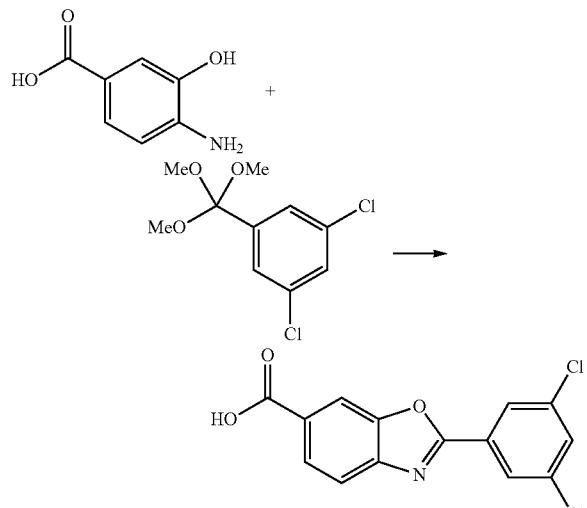

Example 1

4-Amino-3-hydroxybenzoic acid (0.500 g, 3.26 mmol, 1.0 eq) was dissolved in 8.00 mL MeOH and to it was added 1,3-Dichloro-5-(trimethoxymethyl)benzene (0.86 g, 3.4 mmol, 1.05 eq) in 2.00 mL MeOH. The reaction mixture was stirred at RT for 6 h then was heated to 60° C. and stirred overnight. The reaction mixture became a thick slurry. At 23 h, HPLC analysis of the reaction mixture indicated 77.29 area % of the desired product. The reaction mixture was allowed to cool and was filtered. The resulting solids were washed with MeOH (10 mL) and dried under vacuum (65° C., ~50 mbar) to provide 0.531 g (52.8% isolated yield) of the desired product tafamidis as a yellow pink solid.

Example 2

4-Amino-3-hydroxybenzoic acid (0.500 g, 3.26 mmol, 1.0 eq) was dissolved in 8.00 mL MeOH and to it was added TFA (25.0 µL, 0.33 mmol, 0.1 eq) followed by 1,3-Dichloro-5-(trimethoxymethyl)benzene (0.86 g, 3.4 mmol, 1.05 eq) in 2.00 mL MeOH. The reaction mixture was stirred at RT for 6 h then was heated to 60° C. and stirred overnight. The reaction mixture became a thick slurry. At 23 h, HPLC analysis of the reaction mixture indicated 92.19 area % of the desired product. The reaction mixture was allowed to cool and was filtered. The resulting solids were washed with MeOH (10 mL) and dried under vacuum (65° C., ~50 mbar) to provide 0.834 g (82.9% isolated yield) of the desired product tafamidis as a pink solid.

Example 3

4-Amino-3-hydroxybenzoic acid (0.500 g, 3.26 mmol, 1.0 eq) was dissolved in 8.00 mL MeOH and to it was added TFA (63.0 µL, 0.82 mmol, 0.25 eq) followed by 1,3-Dichloro-5-(trimethoxymethyl)benzene (0.86 g, 3.4 mmol, 1.05 eq) in 2.00 mL MeOH. The reaction mixture was stirred at RT for 6 h then was heated to 60° C. and stirred overnight. The reaction mixture became a thick slurry. At 23 h, HPLC analysis of the reaction mixture indicated 91.29 area % of the desired product. The reaction mixture was allowed to cool and was filtered. The resulting solids were washed with MeOH (10 mL) and dried under vacuum (65° C., ~50 mbar) to provide 0.818 g (81.3% isolated yield) of the desired product tafamidis as a pink solid.

Example 4

4-Amino-3-hydroxybenzoic acid (0.500 g, 3.26 mmol, 1.0 eq) was dissolved in 8.00 mL MeOH and to it was added TFA (63.0 µL, 0.82 mmol, 0.25 eq) followed by 1,3-Dichloro-5-(trimethoxymethyl)benzene (0.86 g, 3.4 mmol, 1.05 eq) in 2.00 mL MeOH. The reaction mixture was seeded by addition of tafamidis (50 mg, 0.16 mmol, 0.05 eq). The reaction mixture was stirred at RT for 6 h then was heated to 60° C. and stirred overnight. The reaction mixture became a slurry that was more easily stirred than the slurry obtained in Examples 1-3. At 23 h, HPLC analysis of the reaction mixture indicated 92.36 area % of the desired product. The reaction mixture was allowed to cool and was filtered. The resulting solids were washed with MeOH (10 mL) and dried under vacuum (65° C., ~50 mbar) to provide 0.831 g (82.7% isolated yield) of the desired product as a pink solid.

The reactions for Examples 1-3 were monitored at 1 h, 2 h, 4 h, 7 h and 23 h using high performance liquid chromatography (HPLC) with UV detection. 25 mL of the reaction mixture was sampled and diluted with 975 mL DMSO.

The HPLC chromatographic conditions (Method A) used for monitoring the reaction are as follows:

Column: Agilent Zorbax SB-C18, 1.8 mm, 3.0×50 mm; Column temperature: 50° C.; Mobile Phase A (MPA): 0.05% TFA in water; Mobile Phase B (MPB): Acetonitrile;

Gradient [Time (min), (% MPA/% MPB)]: 0 (95.0/5.0); 1 (95.0/5.0); 9 (0/100); 11.5 (0/100); 11.6 (95.0/5.0); 12.0 (95.0/5.0);

UV detection; Injection volume: 1 mL; Acquisition time: 12 min with 2 min post acquisition.

The chromatographic results indicate that the reactions catalyzed by TFA proceed much faster than the uncatalyzed reaction and are essentially complete after 4 h while the uncatalyzed reaction is not complete at 23 h (see Table 1 below). Seeding of the catalyzed reaction with tafamidis provided a reaction mixture slurry which was more readily stirred than the unseeded reaction mixtures.

TABLE 1

| Example | Retention Time and Area % Tafamidis at 1 h | Retention Time and Area % Tafamidis at 2 h | Retention Time and Area % Tafamidis at 4 h | Retention Time and Area % Tafamidis at 7 h | Retention Time and Area % Tafamidis at 23 h |
|---|---|---|---|---|---|
| 1 | 10.4 | 24.0 | 37.2 | 50.5 | 77.3 |
| 2 | 81.7 | 85.8 | 91.3 | 91.7 | 92.2 |
| 3 | 85.3 | 79.0 | 90.2 | 90.5 | 91.3 |
| 4 | — | — | — | — | 92.4 |

The material obtained from the process was analyzed by 1H, 13C NMR and by LCMS. The results obtained indicate that the desired product tafamidis was obtained.

1H NMR (500 MHz, DMSO-$d_6$) δ $^1$H NMR (500 MHz, DMSO-$d_6$) δ 13.20 (s, 1H), 8.18 (dd, J=1.5, 0.6 Hz, 1H), 8.02 (d, J=1.9 Hz, 2H), 7.97 (dd, J=8.4, 1.5 Hz, 1H), 7.86-7.81 (m, 2H).

13C NMR (126 MHz, DMSO-$d_6$) δ 167.07, 162.35, 150.42, 145.05, 135.58, 132.06, 129.47, 129.16, 126.89, 126.23, 120.36, 112.59.

SQ-LCMS analysis of the product obtained from the instant process was compared with a standard sample of tafamidis free acid and the retention time, molecular ion observed (m/z 308.10 (M+H)) and fragmentation for the product of this process was consistent for tafamidis free acid.

Examples 5-23

The reaction of 4-Amino-3-hydroxybenzoic acid (AHBA) with 1,3-Dichloro-5-(trimethoxymethyl)benzene (Orthoester= "OE") in the presence of 0.25 eq TFA as a catalyst was evaluated in various solvents according to the following general procedure.

AHBA (0.100 g, 0.653 mmol, 1.0 eq) was mixed in 1.50 mL solvent for approximately 1 h and to it was added TFA (12.6 µL, 0.163 mmol, 0.25 eq) and this mixture was stirred for 10 minutes. OE (0.18 g, 0.718 mmol, 1.1 eq) in 0.50 mL solvent was then added to the AHBA mixture. The reaction mixture was heated at 60° C. The reaction mixture was sampled at 1 h, 5 h and 21.5 h and analyzed by HPLC using the previously described HPLC Method A and the area % of the desired product tafamidis was determined (see Table 2 below).

TABLE 2

| Example | Solvent | AHBA Forms Solution? | OE Forms Solution? | Reaction Mixture a Solution at 15 min/at 1 h? | Area % Tafamidis at 1 h | Area % Tafamidis at 5 h | Area % Tafamidis at 21.5 h |
|---|---|---|---|---|---|---|---|
| 5 | Water | No | No | No/No | 0.0 | 23.1 | 91.4 |
| 6 | MeOH | Yes | Yes | No/No | 66.3 | 95.2 | 95.9 |
| 7 | EtOH | Yes | Yes | No/No | 96.3 | 97.4 | 97.4 |
| 8 | IPA | No | No | No/No | 93.2 | 93.5 | 93.2 |
| 9 | n-BuOH | No | No | Yes/No | 92.7 | 94.3 | 94.8 |
| 10 | Acetone | Yes | Yes | No/No | 80.6 | 76.9 | 72.2 |
| 11 | MEK | No | Yes | No/No | 86.0 | 85.1 | 85.5 |
| 12 | THF | Yes | Yes | Yes/Yes | 81.1 | 86.9 | 92.5 |
| 13 | 1,4-Dioxane | Yes | Yes | Yes/No | 81.3 | 86.4 | 86.8 |
| 14 | MTBE | No | No | No/No | 25.3 | 50.6 | 69.1 |
| 15 | Anisole | No | No | No/No | 75.5 | 81.7 | 82.1 |
| 16 | EtOAc | No | No | No/No | 92.1 | 92.3 | 92.5 |
| 17 | Chloroform | No | No | No/No | 24.2 | 36.1 | 52.1 |
| 18 | Chlorobenzene | No | No | No/No | 26.3 | 44.0 | 45.9 |
| 19 | Heptane | No | No | No/No | 36.7 | 71.8 | 82.9 |
| 20 | Cyclohexane | No | No | No/No | 7.0 | 30.2 | 57.8 |
| 21 | Toluene | No | No | No/No | 28.0 | 39.5 | 39.9 |
| 22 | Acetonitrile | No | No | No/No | 94.4 | 94.7 | 95.3 |
| 23 | 1,2-DME | Yes | Yes | Yes / No | 56.3 | 57.4 | 57.1 |

It was found that the reaction progressed rapidly in several solvents. In MeOH, EtOH, IPA, n-BuOH, acetonitrile, acetone, MEK, EtOAc and 1,2-DME the reaction appeared to be essentially complete in one hour or less. However, impurities were observed in the reactions run in EtOH, IPA, n-BuOH, acetone and MEK. The impurities in the reactions where EtOH, IPA or n-BuOH are the solvents may be the corresponding ethyl, isopropyl or n-butyl esters of 3,5-dichlorobenzoic acid, respectively. The reaction was found to proceed more slowly in the ether solvents THF, 1,4-dioxane or MTBE but no significant levels of impurities were observed. In the less polar solvents anisole, chloroform, chlorobenzene, heptane, cyclohexane and toluene the reaction proceeded much more slowly and a significant amount of an impurity with a retention time of 6.1 minutes was observed in each of these reactions. Water is not an ideal solvent since 1,3-Dichloro-5-(trimethoxymethyl)benzene is insoluble in water and can be readily hydrolyzed.

Examples 24-28

In Examples 24-28 the effect of varying amounts of the orthoester, 1,3-Dichloro-5-(trimethoxymethyl)-benzene (1.0, 1.5, 2.0, 5.0 or 10.0 equivalents), on the reaction to form tafamidis was evaluated.

General Procedure

To a solution of TFA (0.0050 mL, 0.065 mmol) in MeOH (4 mL) was added 4-Amino-3-hydroxybenzoic acid, AHBA (0.200 g, 1.31 mmol) followed by addition of 1,3-Dichloro-5-(trimethoxymethyl)-benzene (the orthoester). The reaction mixture was stirred and heated at 60° C. The reaction mixture was sampled at 1 h, 2 h, 5 h and 22 h 40 min and analyzed by HPLC using the previously described HPLC Method A and the area % of the desired product tafamidis was determined. All reactions proceeded quickly and precipitate formed within 15 minutes. Reaction progression was followed by monitoring the disappearance of the AHBA peak. The more ortho ester that was used the quicker the reaction went to completion. Example 24, where 1.0 eq. of the ortho ester was used did not go fully to completion, likely as the result of a small amount of the ortho ester being hydrolyzed to 3,5-Dichlorobenzoic acid methyl ester during the reaction.

The reaction mixtures of Examples 27 and 28, in which 5.0 and 10.0 eq. of ortho ester was used, turned purple. The desired product, tafamidis, was isolated by filtration and the filter cake was washed with methanol. The isolated product obtained from Examples 27 and 28 was slightly pink.

Example 24: Amount of 1,3-Dichloro-5-(trimethoxymethyl)-benzene used was 0.260 mL, 1.31 mmol, 1.0 eq.

Example 25: Amount of 1,3-Dichloro-5-(trimethoxymethyl)-benzene used was 0.390 mL, 1.96 mmol, 1.5 eq.

Example 26: Amount of 1,3-Dichloro-5-(trimethoxymethyl)-benzene used was 0.521 mL, 2.61 mmol, 2.0 eq.

Example 27: Amount of 1,3-Dichloro-5-(trimethoxymethyl)-benzene used was 1.30 mL, 6.52 mmol, 5.0 eq.

Example 28: Amount of 1,3-Dichloro-5-(trimethoxymethyl)-benzene used was 2.60 mL, 13.1 mmol, 10.0 eq.

Results for Examples 24-28 are provided in Table 3 below.

TABLE 3

| Example Number | Ortho ester (eq.) | Isolated mass tafamidis (g) | Isolated Yield (%) |
|---|---|---|---|
| 24 | 1.0 | 0.320 | 79.6 |
| 25 | 1.5 | 0.361 | 89.7 |
| 26 | 2.0 | 0.378 | 94.0 |
| 27 | 5.0 | 0.367 | 91.3 |
| 28 | 10.0 | 0.367 | 91.3 |

Examples 29-33

Examples 29-33 were carried out to determine the effect of varying amounts (5, 10, 25, 50 and 100 mol % in relation to AHBA) of trifluoroacetic acid (TFA) on the reaction of AHBA with 1,3-Dichloro-5-(trimethoxymethyl)-benzene.

General Procedure: A stock solution of TFA (1.263 mL) in MeOH (50 mL) was prepared. MeOH was added to 0.200 g of AHBA (1.31 mmol) followed by addition of the stock solution of TFA in MeOH to provide a total volume of 4.0 mL. To this solution was added 1,3-Dichloro-5-(trimethoxymethyl)benzene (0.286 mL, 1.44 mmol, 1.10 eq.). The reaction mixture was heated to 60° C. and held at this temperature overnight. The reaction mixture was sampled at 0.5 h, 1.0 h, 2.0 h, 5.0 h and 21.25 h and analyzed by HPLC Method A and the area % of the desired product tafamidis was determined. (see Table 4 below).

TABLE 4

| Example Number | Initial Volume MeOH Added to AHBA (mL) | Volume of TFA Stock Solution Added (mL) | Area % Tafamidis at 0.5 h | Area % Tafamidis at 1.0 h | Area % Tafamidis at 2.0 h | Area % Tafamidis at 5.0 h | Area % Tafamidis at 21.25 h |
|---|---|---|---|---|---|---|---|
| 29 | 3.80 | 0.20 (5 mol %) | 27.3 | 40.9 | 75.8 | 78.6 | 92.3 |
| 30 | 3.60 | 0.40 (10 mol %) | 39.5 | 55.9 | 75.3 | 85.8 | 90.8 |
| 31 | 3.00 | 1.00 (25 mol %) | 60.7 | 52.1 | 77.0 | 78.4 | 87.4 |
| 32 | 2.00 | 2.00 (50 mol %) | 61.5 | 63.2 | 66.0 | 73.7 | 77.8 |
| 33 | 0.00 | 4.00 (100 mol %) | 43.6 | 50.6 | 50.7 | 59.3 | 77.3 |

The reactions for Examples 29-33 proceeded quickly with precipitate forming while reaction mixtures were warming, eventually resulting in reaction mixtures which became unstirrable slurries. The reactions of Examples 29 and 30 initially proceeded at a slower rate than Examples 31-33 but went essentially to completion whereas the reactions of Examples 31-33 initially had a faster reaction rate than Examples 29-30 but Examples 31-33 all had unreacted AHBA present at 21.25 h.

Examples 34-46

Examples 34-46 were carried out to determine the effect of either no acid, 10 mol % or 25 mol % of different acids (in relation to AHBA) or 0.75, 1.00 or 1.25 equivalents of triethylamine on the reaction of AHBA with 1,3-Dichloro-5-(trimethoxymethyl)-benzene.

General Procedure: To 150 mg of AHBA (0.979 mmol, 1.0 eq) was added 2.50 mL of MeOH. To this was added either no acid, 10 mol % acid, 25 mol % acid, or 0.75, 1.0 or 1.25 equivalents of TEA (see below for Examples). To this was added 1,3-Dichloro-5-trimethoxymethyl benzene (0.246 g, 0.980 mmol, 1.00 equivalents) in 0.50 mL MeOH.

The reactions of Examples 34-43 was stirred at RT and the reactions of Examples 44-47 was stirred at RT for 6 h then was heated at 60° C. overnight. The reaction mixture was sampled at 1 h, 6 h and as specified in Table 5 and analyzed by HPLC Method A and the area % of the desired product tafamidis was determined. (see Table 5 below).

The reaction mixtures from Examples 34-39 and 42-43 were filtered after 24.25 h and the solids were washed with MeOH (3 mL) and dried under vacuum (65° C., ~50 mbar) to provide tafamidis as a pink solid (yield is provided in Table 5).

Example 34: Acid: TFA, 0.0075 mL, 0.098 mmol, 10 mol %.

Example 35: Acid: TFA, 0.0188 mL, 0.246 mmol, 25 mol %.

Example 36: Acid: HCl in water (12.2 M) 0.0080 mL, 0.098 mmol, 10 mol %.

Example 37: Acid: HCl in water (12.2 M) 0.0201 mL, 0.245 mmol, 25 mol %.

Example 38: Acid: HCl in MeOH (1.0 M) 0.098 mL, 0.098 mmol, 10 mol %.

Example 39: Acid: HCl in MeOH (1.0 M) 0.24 mL, 0.24 mmol, 25 mol %.

Example 40: Acid: AcOH, 0.0056 mL, 0.098 mmol, 10 mol %.

Example 41: Acid: AcOH, 0.0140 mL, 0.244 mmol, 25 mol %.

Example 42: Acid: MeOH, 0.0064 mL, 0.098 mmol, 10 mol %.

Example 43: Acid: MeOH, 0.0161 mL, 0.246 mmol, 25 mol %.

Example 44: Base: TEA, 0.102 mL, 0.732 mmol, 75 mol %.

Example 45: Base: TEA, 0.137 mL, 0.983 mmol, 100 mol %.

Example 46: Base: TEA, 0.171 mL, 1.23 mmol, 125 mol %.

Example 47: no acid or base added.

TABLE 5

| Example | Area % Tafamidis at 1 h | Area % Tafamidis at 6 h | Area % Tafamidis at Time(s) | Yield Tafamidis |
|---|---|---|---|---|
| 34 | 5.0 | 23.6 | 52.6 at 23 h | 0.076 g |
| 35 | 9.7 | 39.8 | 72.6 at 23 h | 0.139 g |
| 36 | 4.1 | 20.8 | 46.5 at 23 h | 0.069 g |
| 37 | 9.2 | 32.7 | 62.1 at 23 h | 0.111 g |
| 38 | 3.1 | 16.1 | 39.9 at 23 h | 0.055 g |
| 39 | 5.1 | 24.3 | 51.7 at 23 h | 0.082 g |
| 40 | none | none | 4.5 at 23 h<br>5.7 at 30 h<br>8.8 at 47 h | — |
| 41 | none | none | 5.5 at 23 h<br>7.2 at 30 h<br>10.9 at 47 h | — |
| 42 | 4.5 | 22.4 | 48.5 at 23 h | 0.077 g |
| 43 | 9.4 | 35.2 | 64.5 at 23 h | 0.124 g |
| 44 | none | none | 7.7 at 16 h<br>10.9 at 23 h<br>17.8 at 40 h | — |
| 45 | none | none | 4.7 at 16 h<br>6.6 at 23 h<br>10.8 at 40 h | — |
| 46 | none | none | 3.1 at 16 h<br>4.4 at 23 h<br>7.1 at 40 h | — |
| 47 | none | none | 3.7 at 23 h<br>5.0 at 30 h<br>7.7 at 47 h | — |

Examples 48-51

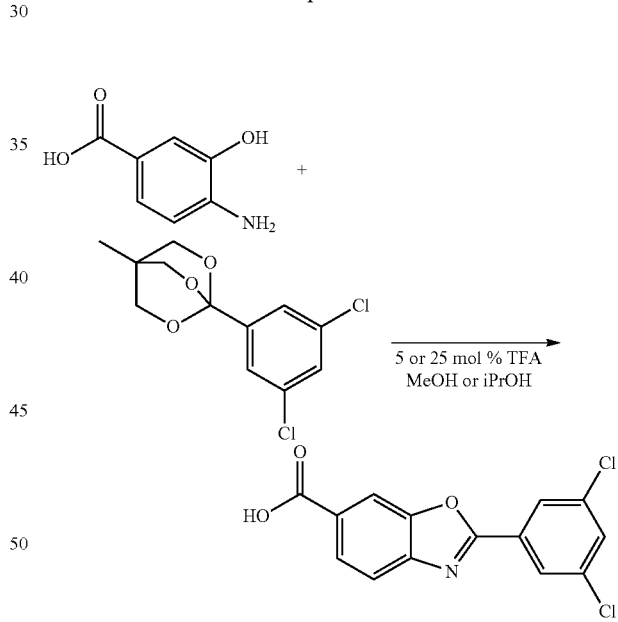

Procedure: Solutions of TFA (316.25 μL) in MeOH (50 mL) and TFA (316.25 μL) in IPA (50 mL) were prepared. In Example 48, 3.20 mL of MeOH was added to AHBA (0.200 g, 1.31 mmol, 1.0 eq.) followed by addition of 0.80 mL of the TFA in MeOH solution (0.065 mmol, 5 mol %) prepared above. In Example 49, 4.0 mL of the TFA in MeOH solution (0.327 mmol, 25 mol %) was added to AHBA (0.200 g, 1.31 mmol, 1.0 eq.). In Example 50, 3.20 mL of IPA was added to AHBA (0.200 g, 1.31 mmol, 1.0 eq.) followed by addition of 0.80 mL of the TFA in IPA solution (0.065 mmol, 5 mol %) prepared above. In Example 51, 4.0 mL of the TFA in IPA solution (0.327 mmol, 25 mol %) was added to AHBA (0.200 g, 1.31 mmol, 1.0 eq.). To each of the mixtures in Examples 48-51 was added the cyclic orthoester, 1-(3,5-Dichlorophenyl)-4-methyl-2,6,7-trioxabicyclo[2.2.2]octane (0.395 g, 1.44 mmol, 1.10 eq.). The reaction mixtures were heated at 60° C. and sampled at 1, 2, 4 and 19.75 h and the Area % tafamidis was determined by HPLC (see Table 6 below). In Example 51 the reaction mixture was filtered and the solids were washed with IPA (4 mL) and dried in a vacuum oven (65° C., ~50 mbar) overnight to provide the desired product tafamidis (0.298 g, 74.1% yield) as a slightly pink solid. 1H NMR and HPLC of the solid obtained from the reaction are consistent for tafamidis.

TABLE 6

| Example | Solvent | mol % TFA | Area % Tafamidis at 1 h | Area % Tafamidis at 2 h | Area % Tafamidis at 4 h | Area % Tafamidis at 19.75 h |
|---|---|---|---|---|---|---|
| 48 | MeOH | 5 mol % | 14.7 | 22.0 | 33.7 | 63.7 |
| 49 | MeOH | 25 mol % | 33.1 | 44.8 | 57.0 | 72.7 |
| 50 | IPA | 5 mol % | 39.6 | 52.7 | 65.6 | 85.5 |
| 51 | IPA | 25 mol % | 65.2 | 74.7 | 82.1 | 88.5 |

The reactions in IPA progressed more quickly than the reactions in MeOH with the reactions in IPA close to completion at 19.75 h.

Example 52

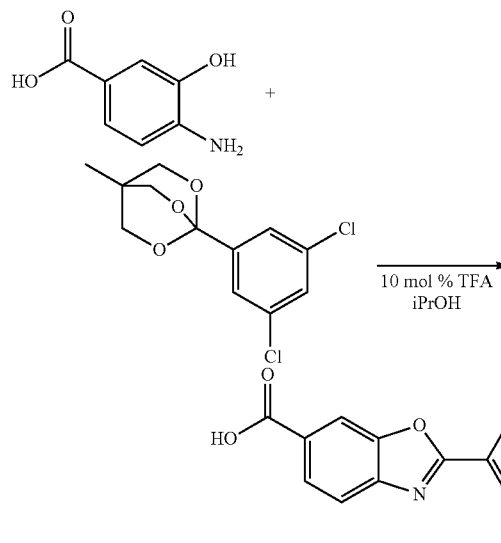

To 8 mL of IPA at 20° C. with stirring was added 4-Amino-3-hydroxybenzoic acid (401 mg, 2.62 mmol) and 1-(3,5-Dichlorophenyl)-4-methyl-2,6,7-trioxabicyclo[2.2.2]octane (795 mg, 2.89 mmol) followed by TFA (30 μL, 0.388 mmol). The reaction mixture was heated to 85° C. and stirred at that temperature for 12 h. The mixture was then cooled to 20° C. and batch granulated at 20° C. for 2 h. The resulting solid was collected by filtration and was rinsed with IPA that was used to wash the reaction vessel (2×4 mL). The resulting pink solid was dried under vacuum (50 mbar) at 60° C. for 12 h to provide tafamidis (637 mg, 2.068 mmol, 79% yield). 1H NMR, LC-MS and LC-MS/MS when compared to standard were obtained and were consistent for the desired product tafamidis. LC-MS used to monitor reaction completion showed 76.7% peak area tafamidis prior to isolation.

Example 53

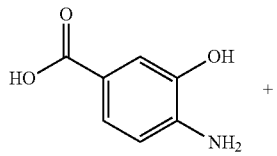

-continued

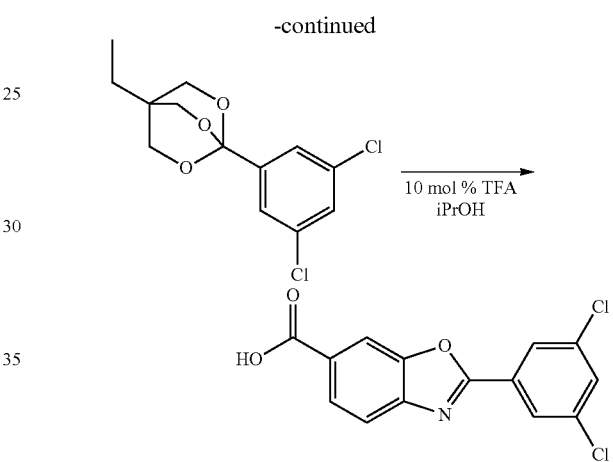

To 8 mL of IPA at 20° C. with stirring was added 4-Amino-3-hydroxybenzoic acid (402 mg, 2.62 mmol) and 1-(3,5-Dichlorophenyl)-4-ethyl-2,6,7-trioxabicyclo[2.2.2]octane (832 mg, 2.88 mmol) followed by TFA (30 μL 0.388 mmol). The reaction mixture was heated to 85° C. and stirred at that temperature for 12 h. The mixture was then cooled to 20° C. and batch granulated at 20° C. for 2 h. The resulting solid was collected by filtration and was rinsed with IPA that was used to wash the reaction vessel (2×4 mL). The resulting pink solid was dried under vacuum (50 mbar) at 60° C. for 12 h to provide tafamidis (564 mg, 1.83 mmol, 69.9% yield). 1H NMR, LC-MS and LC-MS/MS when compared to standard were consistent for the desired product tafamidis. LC-MS used to monitor reaction completion showed 65.4% peak area tafamidis prior to isolation.

Example 54

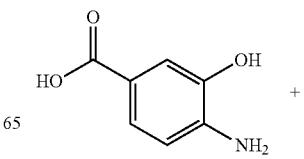

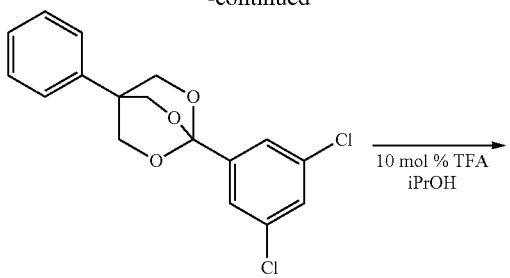

To 8 mL of IPA at 20° C. with stirring was added 4-Amino-3-hydroxybenzoic acid (405 mg, 2.65 mmol) and 1-(3,5-Dichlorophenyl)-4-phenyl-2,6,7-trioxabicyclo[2.2.2]octane (974 mg, 2.89 mmol) followed by TFA (30 µL, 0.388 mmol). The reaction mixture was heated to 85° C. and stirred at that temperature for 12 h. The mixture was then cooled to 20° C. and batch granulated at 20° C. for 2 h. The resulting solid was collected by filtration and was rinsed with IPA that was used to wash the reaction vessel (2×4 mL). The resulting pink solid was dried under vacuum (50 mbar) at 60° C. for 12 h to provide tafamidis (591 mg, 1.92 mmol, 72.5% yield). 1H NMR, LC-MS and LC-MS/MS when compared to standard were consistent for the desired product tafamidis. LC-MS used to monitor reaction completion showed 65.5% peak area tafamidis prior to isolation.

Example 55

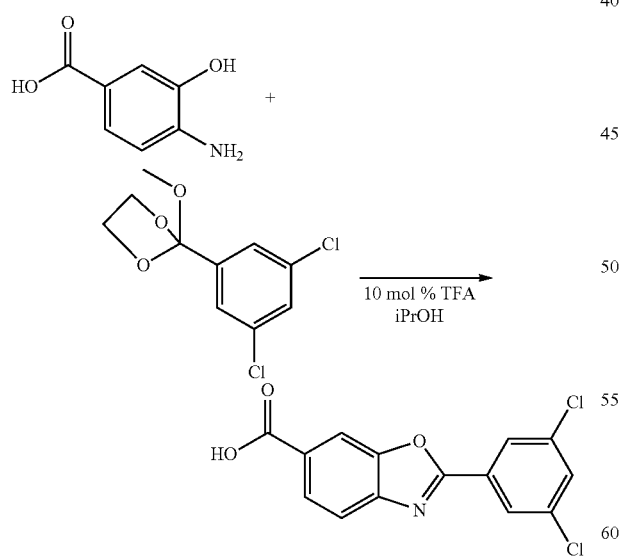

To 8 mL of IPA at 20° C. with stirring was added 4-Amino-3-hydroxybenzoic acid (402 mg, 2.62 mmol) and 2-(3,5-Dichlorophenyl)-2-methoxy-1,3-dioxolane (735 mg, 2.95 mmol) followed by TFA (30 µL, 0.388 mmol). The reaction mixture was heated to 85° C. and stirred at that temperature for 12 h. The mixture was then cooled to 20° C. and batch granulated at 20° C. for 2 h. The resulting solid was collected by filtration and was rinsed with IPA that was used to wash the reaction vessel (2×4 mL). The resulting pink solid was dried under vacuum (50 mbar) at 60° C. for 12 h to provide tafamidis (701 mg, 2.28 mmol, 86.7% yield). 1H NMR, LC-MS and LC-MS/MS when compared to standard were consistent for the desired product tafamidis. LC-MS used to monitor reaction completion showed 88.9% peak area tafamidis prior to isolation.

Example 56

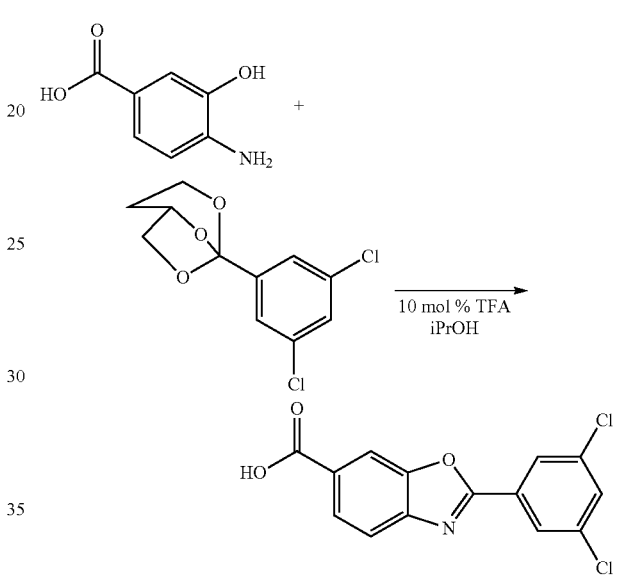

To 8 mL of IPA at 20° C. with stirring was added 4-Amino-3-hydroxybenzoic acid (402 mg, 2.65 mmol) and 1-(3,5-Dichlorophenyl)-2,7,8-trioxabicyclo[3.2.1]octane (761 mg, 2.91 mmol) followed by TFA (30 µL, 0.388 mmol). The reaction mixture was heated to 85° C. and stirred at that temperature for 12 h. The mixture was then cooled to 20° C. and batch granulated at 20° C. for 2 h. The resulting solid was collected by filtration and was rinsed with IPA that was used to wash the reaction vessel (2×4 mL). The resulting pink solid was dried under vacuum (50 mbar) at 60° C. for 12 h to provide tafamidis (679 mg, 2.20 mmol, 84.0% yield). 1H NMR, LC-MS and LC-MS/MS when compared to standard were consistent for the desired product tafamidis. LC-MS used to monitor reaction completion showed 78.5% peak area tafamidis prior to isolation.

Example 57

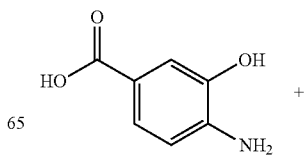

37

-continued

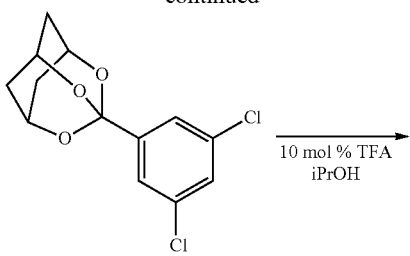

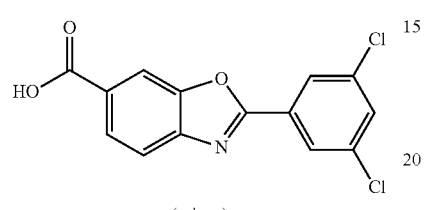
(minor)

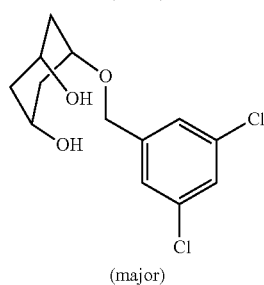
(major)

To 8 mL of IPA at 20° C. with stirring was added 4-Amino-3-hydroxybenzoic acid (400 mg, 2.61 mmol) and 3-(3,5-Dichlorophenyl)-2,4,10-trioxaadamantane (842 mg, 2.93 mmol) followed by TFA (30 μL, 0.388 mmol). The reaction mixture was heated to 85° C. and stirred at that temperature for 12 h. The mixture was then cooled to 20° C. and batch granulated at 20° C. for 2 h. The resulting solid was collected by filtration and was rinsed with IPA that was used to wash the reaction vessel (2×4 mL). The resulting solid was dried under vacuum (50 mbar) at 60° C. for 12 h to provide a solid (692 mg). Analysis of this solid by 1H NMR and LC-MS indicated it was primarily ring opened 3-(3,5-Dichlorophenyl)-2,4,10-trioxaadamantane depicted above as the major component and LC-MS/MS analysis indicating the desired product tafamidis was present as a minor component. Presumably, the ring strain of the starting 3-(3,5-Dichlorophenyl)-2,4,10-trioxaadamantane results in hydrolysis of this material being favorable to the reaction leading to formation of tafamidis.

Example 58

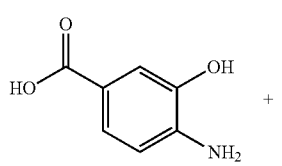

38

-continued

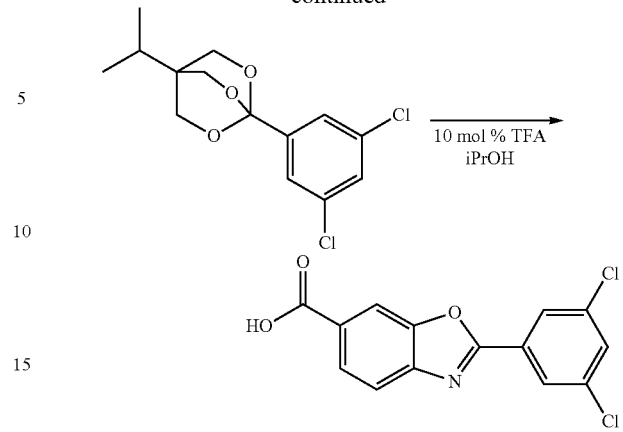

To 8 mL of IPA at 20° C. with stirring is added 4-Amino-3-hydroxybenzoic acid (402 mg, 2.62 mmol) and 1-(3,5-dichlorophenyl)-4-isopropyl-2,6,7-trioxabicyclo[2.2.2]octane (2.88 mmol) followed by TFA (30 L1, 0.388 mmol). The reaction mixture is heated to 85° C. and stirred at that temperature for 12 h. The mixture is cooled to 20° C. and batch granulated at 20° C. for 2 h. The resulting solid is collected by filtration and is rinsed with IPA that is used to wash the reaction vessel (2×4 mL). The resulting solid is dried under vacuum (50 mbar) at 60° C. for 12 h to provide tafamidis. 1H NMR, LC-MS and LC-MS/MS is compared to a tafamidis standard sample.

Example 59

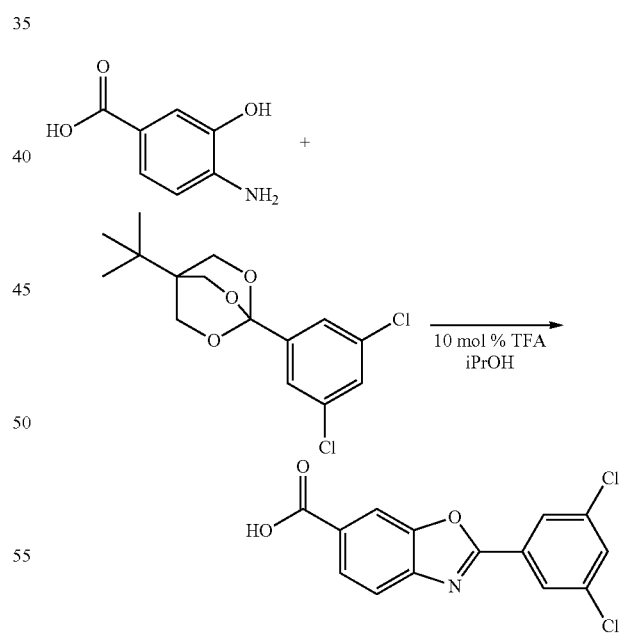

To 8 mL of IPA at 20° C. with stirring is added 4-Amino-3-hydroxybenzoic acid (402 mg, 2.62 mmol) and 4-(tert-butyl)-1-(3,5-dichlorophenyl)-2,6,7-trioxabicyclo[2.2.2]octane (2.88 mmol) followed by TFA (30 μL, 0.388 mmol). The reaction mixture is heated to 85° C. and stirred at that temperature for 12 h. The mixture is cooled to 20° C. and batch granulated at 20° C. for 2 h. The resulting solid is collected by filtration and is rinsed with IPA that is used to wash the reaction vessel (2×4 mL). The resulting solid is dried under vacuum (50 mbar) at 60° C. for 12 h to provide tafamidis. 1H NMR, LC-MS and LC-MS/MS is compared to a tafamidis standard sample.

The invention claimed is:

1. A process for preparing a 6-Carboxy-2-(3,5-dichlorophenyl)benzoxazole compound of Formula I

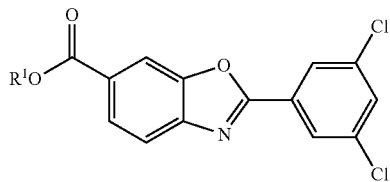

the process comprising reacting a 4-Amino-3-hydroxybenzoic acid compound of Formula III with a 3,5-Dichlorophenyl ortho ester compound of Formula II in the presence of an acid catalyst in a solvent to provide the compound of Formula I

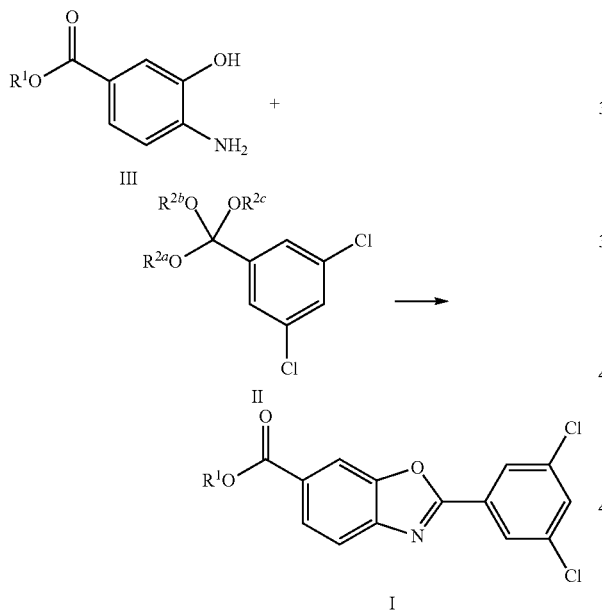

wherein $R^1$ is hydrogen or a carboxy protecting group, and $R^{2a}$, $R^{2b}$ and $R^{2c}$ are each independently $C_1$-$C_6$alkyl or any two of $R^{2a}$, $R^{2b}$ and $R^{2c}$ taken together are a $C_1$-$C_6$alkanediyl or $R^{2a}$, $R^{2b}$ and $R^{2c}$ taken together are a $C_3$-$C_{10}$alkanetriyl; and the solvent is selected from the group consisting of methanol, ethanolisopropanol, n-butanol, acetone, methyl ethyl ketone, tetrahydrofuran, 1,4-dioxane, t-butyl methyl ether, anisole, ethyl acetate, chloroform, chlorobenzene, heptane, cyclohexane, toluene, acetonitrile and 1,2-dimethoxyethane.

2. The process of claim 1 wherein the reaction of the compound of Formula III with the compound of Formula II to provide the compound of Formula I is carried out in the presence of an acid catalyst selected from the group consisting of trifluoroacetic acid, acetic acid, hydrochloric acid and methanesulfonic acid.

3. The process of claim 1 wherein the reaction of the compound of Formula III with the compound of Formula II to provide the compound of Formula I is carried out at a temperature of about room temperature to about 100° C.

4. The process of claim 3 wherein the temperature is about room temperature to about 65° C.

5. The process of claim 1 wherein the reaction of the compound of Formula III with the compound of Formula II to provide the compound of Formula I is carried out for a period of about 0.25 hours to about 40 hours.

6. The process of claim 1 wherein $R^1$ is hydrogen.

7. The process of claim 1 wherein $R^{2a}$, $R^{2b}$ and $R^{2c}$ are each independently $C_1$-$C_6$alkyl.

8. The process of claim 7 wherein $R^{2a}$, $R^{2b}$ and $R^{2c}$ are each methyl.

9. The process of claim 1 wherein $R^{2a}$, $R^{2b}$ and $R^{2c}$ taken together are a $C_3$-$C_{10}$alkanetriyl.

10. The process of claim 9 wherein the compound of Formula II is

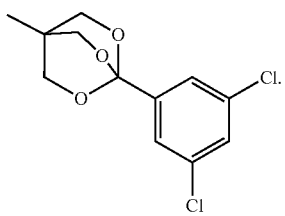 [SMILES: CC12COC(c3cc(Cl)cc(Cl)c3)(OC1)OC2]

11. The process of claim 1 further comprising the step of isolating the compound of Formula I.

12. The process of claim 11 wherein the compound of Formula I is isolated by filtration.

13. A process for preparing 6-Carboxy-2-(3,5-dichlorophenyl)benzoxazole of Formula Ia

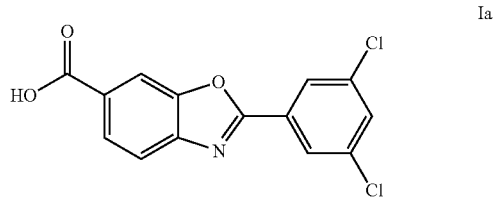 [SMILES: O=C(O)c1ccc2nc(-c3cc(Cl)cc(Cl)c3)oc2c1]

the process comprising reacting 4-Amino-3-hydroxybenzoic acid of Formula IIIa with a 3,5-Dichlorophenyl ortho ester compound of Formula II in the presence of an acid catalyst in a solvent to provide 6-Carboxy-2-(3,5-dichlorophenyl)benzoxazole of Formula Ia

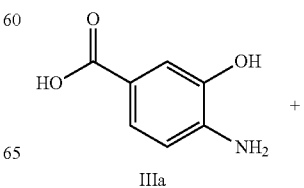

-continued

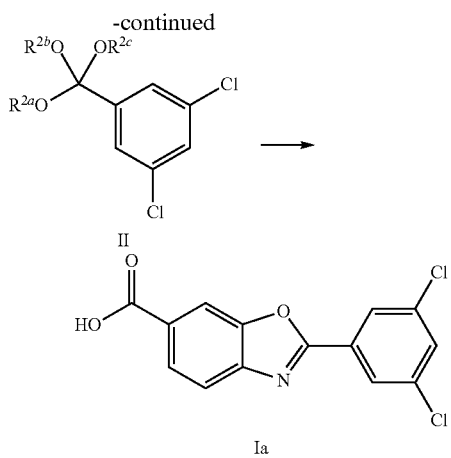

wherein $R^{2a}$, $R^{2b}$ and $R^{2c}$ are each independently $C_1$-$C_6$alkyl or any two of $R^{2a}$, $R^{2b}$ and $R^{2c}$ taken together are a $C_1$-$C_6$alkanediyl or $R^{2a}$, $R^{2b}$ and $R^{2c}$ taken together are a $C_3$-$C_{10}$alkanetriyl; and the solvent is selected from the group consisting of methanol, ethanol, isopropanol, n-butanol, acetone, methyl ethyl ketone, tetrahydrofuran, 1,4-dioxane, t-butyl methyl ether, anisole, ethyl acetate, chloroform, chlorobenzene, heptane, cyclohexane, toluene, acetonitrile and 1,2-dimethoxyethane.

14. The process of claim 13 wherein the reaction of the compound of Formula IIIa with the compound of Formula II to provide the compound of Formula Ia is carried out in the presence of an acid catalyst selected from the group consisting of trifluoroacetic acid, acetic acid, hydrochloric acid and methanesulfonic acid.

15. The process of claim 13 wherein the reaction of the compound of Formula III with the compound of Formula II to provide the compound of Formula I is carried out at a temperature of about room temperature to about 100° C.

16. The process of claim 15 wherein the temperature is about room temperature to about 65° C.

17. The process of claim 13 wherein the reaction of the compound of Formula III with the compound of Formula II to provide the compound of Formula I is carried out for a period of about 0.25 hours to about 40 hours.

18. The process of claim 13 wherein $R^{2a}$, $R^{2b}$ and $R^{2c}$ are each independently $C_1$-$C_6$alkyl.

19. The process of claim 18 wherein $R^{2a}$, $R^{2b}$ and $R^{2c}$ are each methyl.

20. The process of claim 13 wherein $R^{2a}$, $R^{2b}$ and $R^{2c}$ taken together are a $C_3$-$C_{10}$alkanetriyl.

21. The process of claim 20 wherein the compound of Formula II is

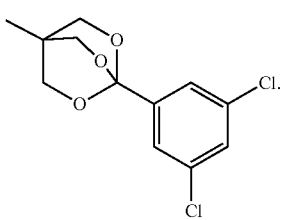

22. The process of claim 13 further comprising the step of isolating the compound of Formula Ia.

23. The process of claim 22 wherein the compound of Formula Ia is isolated by filtration.

24. The process of claim 13 further comprising the step of reacting the 6-Carboxy-2-(3,5-dichlorophenyl)benzoxazole of Formula Ia with a pharmaceutically acceptable base to provide a pharmaceutically acceptable salt of 6-Carboxy-2-(3,5-dichlorophenyl)benzoxazole.

25. The process of claim 24 wherein the 6-Carboxy-2-(3,5-dichlorophenyl) benzoxazole is reacted with meglumine in an appropriate solvent to provide 6-Carboxy-2-(3,5-dichlorophenyl)benzoxazole meglumine salt.

26. The process of claim 25 wherein 6-Carboxy-2-(3,5-dichlorophenyl) benzoxazole is reacted at room temperature with meglumine in a solvent selected from methyl isobutyl ketone, MTBE and EtOAc and the resulting solid is isolated and dried to provide the Form E polymorph of 6-Carboxy-2-(3,5-dichlorophenyl)benzoxazole meglumine salt.

27. The process of claim 25 wherein the 6-Carboxy-2-(3,5-dichlorophenyl) benzoxazole is reacted with meglumine in a mixture of IPA and water and the resulting solid is isolated and dried to provide the Form M polymorph of 6-Carboxy-2-(3,5-dichlorophenyl)benzoxazole meglumine salt.

28. The process of claim 22 further comprising the step of stirring the compound of Formula Ia in a mixture of water and IPA then isolating and drying the resulting solid to provide the Form 1 polymorph of 6-Carboxy-2-(3,5-dichlorophenyl)benzoxazole.

29. A process for preparing 6-Carboxy-2-(3,5-dichlorophenyl)benzoxazole of Formula Ia

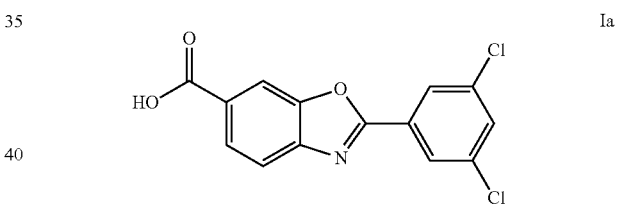

the process comprising reacting about one molar equivalent of 4-Amino-3-hydroxybenzoic acid of Formula IIIa with about one molar equivalent of the 3,5-Dichlorophenyl ortho ester compound of Formula IIa in a solvent to provide 6-Carboxy-2-(3,5-dichlorophenyl)benzoxazole of Formula Ia

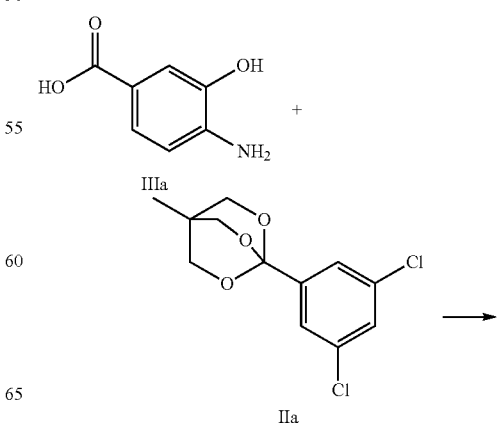

-continued

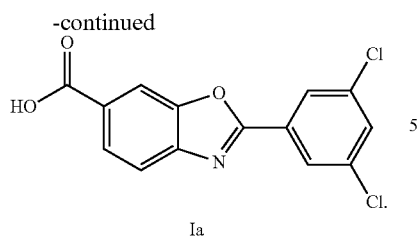

Ia

30. The process of claim 29 wherein the solvent is selected from the group consisting of methanol, ethanol, isopropanol, n-butanol, acetone, methyl ethyl ketone, tetrahydrofuran, 1,4-dioxane, t-butyl methyl ether, anisole, ethyl acetate, chloroform, chlorobenzene, heptane, cyclohexane, toluene, acetonitrile and 1,2-dimethoxyethane.

31. The process of claim 30 wherein the solvent is selected from the group consisting of methanol, isopropanol, acetonitrile, ethyl acetate, 1,2-dimethoxyethane, tetrahydrofuran, t-butyl methyl ether and 1,4-dioxane.

32. The process of claim 31 wherein the process is carried out using an acid catalyst selected from the group consisting of trifluoroacetic acid, acetic acid, hydrochloric acid and methanesulfonic acid.

33. The process of claim 31 wherein the acid catalyst is trifluoroacetic acid and the solvent is isopropanol.

* * * * *